United States Patent [19]
Kasukabe et al.

[11] Patent Number: 6,166,294
[45] Date of Patent: *Dec. 26, 2000

[54] COTTON FIBER TISSUE-SPECIFIC GENES

[75] Inventors: Yoshihisa Kasukabe; Koichi Fujisawa; Susumu Nishiguchi; Yoshihiko Maekawa, all of Otsu, Japan; Randy Dale Allen, Lubbock, Tex.

[73] Assignees: Toyobo Co., LTD, Osaka-fu, Japan; Texas Tech University, Lubbock, Tex.

[*] Notice: This patent is subject to a terminal disclaimer.

[21] Appl. No.: 09/262,653

[22] Filed: Mar. 4, 1999

Related U.S. Application Data

[63] Continuation of application No. 08/580,545, Dec. 29, 1995, Pat. No. 5,932,713, which is a continuation-in-part of application No. 08/391,696, Feb. 21, 1995, Pat. No. 5,880,110.

[51] Int. Cl.[7] .............................. A01H 5/00; C07H 21/04; C12N 15/82
[52] U.S. Cl. ..................... 800/298; 435/320.1; 536/23.6; 536/24.5; 800/278; 800/286
[58] Field of Search ................................... 536/23.6, 24.5; 435/69.1, 320.1, 419, 468; 800/278, 286, 290, 298, 314

[56] References Cited

U.S. PATENT DOCUMENTS 5,932,713  8/1999  Kasukabe et al. .................... 536/23.6

OTHER PUBLICATIONS

John Me, et al. "Gene expression in cotton (Gossypium hirsutum L.) fiber: Cloning of the mRNAs." PNAS 89: 5769–5773, Jul. 1992.

*Primary Examiner*—Amy J. Nelson
*Attorney, Agent, or Firm*—Morrison & Forester, LLP

[57] ABSTRACT

Cotton fiber tissue-specific genes disclosed herein are specifically expressed in a cotton fiber tissue at the stage of cotton fiber elongation. One of the genes was first derived from a cotton plant of the genus Gossypium and found to change the degree of its expression by treatment with a brassinosteroid.

6 Claims, 12 Drawing Sheets

NORTHERN BLOTTING

Tissue specificity of KC18 gene expression 1. 10DPA INTACT OVULE
2. MATURE SEED
3. 18DAYS SEEDLING
4. LEAF 5. 10DPA INTACT OVULE
6. 14DPA FIBER
7. 14DPA STRIPPED OVULE
8. 22DPA FIBER
9. 22DPA STRIPPED OVULE

NORTHERN BLOTTING

Tissue specificity of KC22 gene expression 1. 10DPA INTACT OVULE
2. MATURE SEED
3. 18DAYS SEEDLING
4. LEAF 5. 10DPA INTACT OVULE
6. 14DPA FIBER
7. 14DPA STRIPPED OVULE
8. 22DPA FIBER
9. 22DPA STRIPPED OVULE

NORTHERN BLOTTING

Tissue specificity of KC03 gene expression 1. 10DPA INTACT OVULE
2. MATURE SEED
3. 18DAYS SEEDLING
4. LEAF 5. 10DPA INTACT OVULE
6. 14DPA FIBER
7. 14DPA STRIPPED OVULE
8. 22DPA FIBER
9. 22DPA STRIPPED OVULE RNA blot analysis of differential tissues.

RNA blot analysis of intact ovules at different days after anthesis.

Northern Analysis: pKC22
RNA: 7 Days Post Anthesis

(1)  (2)  (3)

1) In vivo fiber RNA from Coker-312
2) In vitro fiber RNA with $10^{-6}$M Brassinolide
3) In vitro fiber RNA control CONSTRUCTION OF pBI35S-22(+)    FIG.10

Photographs of typical transgenic *Arabidopsis thaliana* WS plants at 8 weeks
(A) Right; transgenic 1-5 (35S:KC22 sense) and left; wild type
(B) Right; transgenic 3-4 (35S:KC22 antisense) and left; wild type

COTTON FIBER TISSUE-SPECIFIC GENES

CROSS-REFERENCE TO RELATED APPLICATIONS

The present application is a continuation of application of U.S. Ser. No. 08/580,545 filed on Dec. 29, 1995, issued as U.S. Pat. No. 5,932,713, which is a continuation-in-part application of U.S. Ser. No. 08/391,696 filed on Feb. 21, 1995, issued as U.S. Pat. No. 5,880,110.

FIELD OF THE INVENTION

The present invention relates to genes which are specifically expressed in a cotton fiber tissue at the stage of cotton fiber elongation, anti-sense genes of said genes, and their use. The present invention further relates to a gene derived from a cotton plant, capable of changing the degree of its expression by treatment with a brassinosteroid, an anti-sense gene of said gene, and their use.

BACKGROUND OF THE INVENTION

Usually, cotton fibers are produced by cultivating a cotton plant of the genus Gossypium and collecting the cotton fibers from the capsules (cotton bolls) formed on the cotton plant. There are many varieties of cotton plant, from which cotton fibers with different fiber characteristics can be obtained and used for various applications depending on their fiber characteristics. Cotton fibers are characterized by various properties among which fiber length, fiber fineness and fiber strength are particularly important. Many previous efforts have been made to improve the characteristics of cotton fibers. Attempted improvements have been mainly focused on fiber length and fiber fineness. In particular, there has been a great demand for longer and finer cotton fibers. The variety of cotton plant known as Sea Island is famous for desired fiber characteristics; however, this variety of cotton plant exhibits a poor yield of cotton fibers, therefore the price of Sea Island cotton fibers is very high. If highly yielding cotton plants with fiber characteristics equal to or better than those of Sea Island cotton can be produced, it will be a great contribution to industry.

The methods for improving the characteristics or yield of cotton fibers can be roughly classified into the following three categories:

1. Variety Improvement by Cross Breeding

This method has been utilized most widely so far. At present, almost all the cultivated varieties of cotton plant were bred by this method. However, much time is needed for this method, and because of a limit to the degree of variability, one cannot expect remarkable improvements in fiber characteristics or in yield of cotton fibers.

2. Treatment with Plant Hormone

Plant hormones such as auxin, gibberellin, cytokinin and ethylene have been widely applied to field crops or horticultural products. Many reports have hitherto been made with respect to the influence of plant hormones on the fiber production of cotton plants, particularly on the fiber elongation mechanism. It is believed that fiber elongation is induced by gibberellin or auxin but inhibited by abscisic acid (Bhardwaj and Sharma, 1971; Singh and Sing, 1975; Baert et al., 1975; Dhindsa et al., 1976; Kosmidou, 1976; Babaev and Agakishiev, 1977; Bazanova, 1977; DeLanghe et al., 1978). Also Beasley and Ting [Amer. J. Bot., 60(2): 130–139 (1973)] reported that gibberellin has a promoting effect on the fiber elongation in ovule cultures (in vitro) whereas kinetin and abscisic acid have an inhibitory effect on the fiber elongation.

In a field test (in vivo), when non-fertilized flowers of cotton plants were treated with gibberellin just after flowering, there was found a promoting effect on the fiber elongation to a certain degree; in the case of fertilized flowers, however, no significant promotion was caused by gibberellin treatment (The Cotton Foundation Reference Book, Series Number 1, Cotton Physiology, 369, The Cotton Foundation, 1986).

As to the influence of plant hormones on the yield of cotton fibers was analyzed by MaCarty and Hedin who reported as follows: a field test on commercial plant growth regulators were carried out for a period of from 1986 to 1992. They found only in the field test of 1992 that an increase in fiber yield was observed with a Foliar Trigger (manufactured by Westbridge Chemical Co.) containing cytokinin or with FPG-5 (manufactured by Baldridge Bio-Research, Inc.) containing cytokinin, indoleacetic acid and gibberellin; however, no significant increase in fiber yield was observed in the other years [J. Agric. Food Chem., 42: 1355–1357 (1994)].

As described above, for the purpose of improving the characteristics and yield of cotton fibers, a number of studies and reports have been made on conventional plant hormones such as auxin, gibberellin, cytokinin and abscisic acid; however, no effect has been fully confirmed yet, and it cannot be said that these plant hormones are effective for practical use.

In recent years, much attention has been paid to brassinosteroids as a novel group of plant hormones, and the action of these hormones on various plants has been studied. For the first time, Mitchell, Mandave, et al., discovered brassinolide, which is one of the brassinosteroids, from *Brassica napus* pollen [Nature, 225, 1065 (1970)], and they confirmed that it has a remarkable effect on the cell elongation in the young buds of kidney bean. As described above, brassinolide is one of the steroid compounds with complicated structure, and many compounds with structural similarities thereto have since been discovered from various plants.

The effects of brassinosteroid when applied to cotton plants, was reported by Luo et al. [Plant Physiology Communications, 5: 31–34 (1988)] that the treatment of boll stalks with 0.01 or 1 ppm brassinolide reduced the shedding of young bolls in a field test (in vivo). However, no report has hitherto been made that the characteristics or yield of cotton fibers can be improved by the use of any brassinosteroid.

For callus culture (in vitro), Wang et al. [Plant Physiology Communications, 28(1): 15–18 (1992)] reported that the addition of 0.01 ppm brassinolide to MS medium induced the callus formation and embryogenesis in cotton plants. However, no report has hitherto been made that the characteristics or yield of cotton fibers can be improved by addition of a brassinosteroid to a medium used for the ovule culture in the production of cotton fibers.

3. Variety Improvement by Gene Recombination Technique

In recent years, gene recombinant technique has made startling progress, and several reports have been made on the successful variety improvement in certain kinds of plants (e.g., cotton, tomato, soybean) by introduction and expression of a particular gene in these plants to confer a desired genetic trait thereon. For example, the following studies have been made on cotton plants: one is to improve insect resistance by introduction of a gene coding for BT toxin (*Bacillus thuringiensis* produced insecticidal protein toxin), and the other is to improve herbicide (Glyphosate) resistance by introduction of a gene coding for 5-enolpyruvilshikimic acid 3-phosphate synthetase.

If a gene associated with fiber formation and elongation can be introduced into cotton plants and expressed in large quantities, it would become possible to make a remarkable improvement in the characteristics or yield of cotton fibers. Further, the introduction of such a gene in anti-sense form makes it possible to suppress the action of this gene. In other words, it is believed that the characteristics and yield of cotton fibers can be controlled by introducing a gene associated with fiber formation and elongation into cotton plants, followed by large-scale expression or suppression of the gene. The method using such a genetic engineering technique can be expected to find wide applications, e.g., more reliable fiber elongation control as compared with the conventional plant breeding by crossbreeding and screening. For this purpose, a gene associated with fiber elongation, which is greatly expressed in a fiber tissue-specific manner at the fiber elongation stage, must be isolated and identified.

At present, however, the knowledge of fiber elongation in plants from the viewpoint of molecular biology is very limited. Although many studies have been made on the elongation of plant cells, most of the control factors remain unknown and the control mechanisms have not yet been elucidated. This is, for example, because a gene expressed specifically in the fiber elongation stage and also in the elongating fiber tissue is difficult to obtain and examine for its function.

A cotton fiber is composed of a single cell differentiated from an epidermal cell of the seed coat and develops though four stages, i.e., initiation, elongation, secondary cell wall thickening and maturation stages. More particularly, an epidermal cell of the ovule begins cotton fiber elongation just after flowering, and a cotton fiber rapidly elongates and completes elongation in about 25 days after flowering. Then, fiber elongation stops, and a secondary cell wall is formed and grown to become a mature cotton fiber. It seems that the examination of the expression of a gene in the ovule, particularly in the cotton fiber tissue, at the fiber elongation stage in the fiber growth process is an effective means of elucidating the mechanism of fiber elongation.

Several attempts have been made on such an isolation of genes from cotton fibers. Many of the genes actively functioning in the fiber cell are closely similar to those which are present in the leaf, ovule or root. The isolation of a gene expressed preferentially in a cotton fiber tissue was reported by Maliykal E. John and Laura J. Crow [Proc. Natl. Acad. Sci. USA, 89, 5769 (1992)]. However, only a few reports have been made on the cotton fiber tissue-specific gene.

In recent years, an effective method for isolating a gene which is specifically expressed in different cells or under the particular conditions, i.e., differential display method, was reported. However, there has been no report on the isolation of a cotton fiber tissue-specific gene using the differential display method.

SUMMARY OF THE INVENTION

Under these circumstances, the present inventors have intensively studied to improve the characteristics and yield of cotton fibers. As a result, they have discovered a cotton plant gene capable of changing the degree of its expression by treatment with a brassinosteroid, which is then found to be, associated with the formation and elongation of cotton fibers, and after further studies, they have succeeded in isolation and identification of cotton fiber tissue-specific genes, thereby completing the present invention.

Thus, the present invention provides a gene derived from a cotton plant of the genus Gossypium, capable of changing the degree of its expression by treatment with a brassinosteroid, as well as several cotton fiber tissue-specific genes which are specifically expressed in a cotton fiber tissue at the stage of fiber elongation. One of these cotton fiber tissue-specific genes is found to have the same nucleotide sequence as that of the cotton plant gene capable of changing the degree of its expression by treatment with a brassinosteroid.

The present invention further provides various genes derived from the above genes, e.g., genes capable of hybridizing with the above genes, anti-sense genes to the above genes; recombinant vectors containing the above genes; transformants obtained by transformation of these recombinant vectors; proteins obtained by expression of the above genes; and methods for producing cotton fibers by utilization of the above genes.

DETAILED DESCRIPTION OF THE INVENTION

Figure 1:
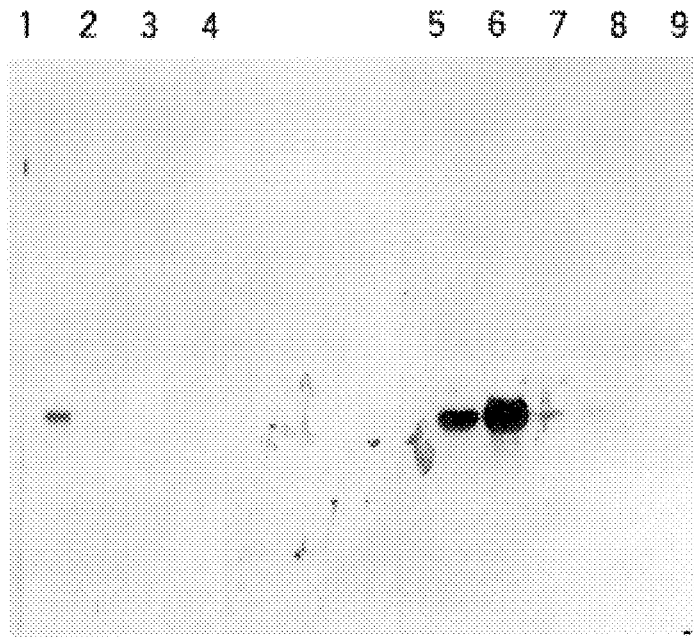
FIG. 1 is a photograph showing the results of Northern blotting of KC18. The tissue specificity of KC18 gene expression was revealed; lane 1, intact ovule on the 10th day after the flowering; lane 2, mature seed; lane 3, seedling after 18 days; lane 4, leaf; lane 5, intact ovule on the 10th day after the flowering; lane 6, fiber on the 14th day after the flowering; lane 7, stripped ovule on the 14th day after the flowering; lane 8, fiber on the 22nd day after the flowering; and lane 9, stripped ovule on the 22nd day after the flowering.

The term "cotton fiber tissue-specific gene" as used herein refers to a gene which is specifically expressed in a cotton fiber tissue at the fiber elongation stage. The term "cotton fiber tissue" as used herein refers to any one of the cotton fiber tissues at different fiber development stages, extending from a slightly elongating epidermal cell of the ovule just after the flowering to a mature cotton fiber. The term "stage of cotton fiber elongation" or "(cotton) fiber elongation stage" as used herein refers to a period of time extending from just after the flowering to the 25th day after the flowering (post-anthesis).

The cotton fiber tissue-specific genes of the present invention include various genes capable of hybridizing with a gene which is specifically expressed in a cotton fiber tissue at the stage of cotton fiber elongation, under the conditions that the hybridization is carried out at 50° C. with a solution containing 6×SSC (0.9 M NaCl, 0.09 M trisodium citrate).

Typical examples of the cotton fiber tissue-specific genes are those which code for the amino acid sequence of SEQ ID NO: 2, 4, 6, 8, or 10; and these genes have, for example, the nucleotide sequence of SEQ ID NO: 1, 3, 5, 7 or 9.

The term "anti-sense gene" as used herein refers to a gene having a complementary sequence to the nucleotide sequence of a cotton fiber tissue-specific gene which is specifically expressed in a cotton fiber tissue at the stage of cotton fiber elongation, e.g., an anti-sense DNA complimentary to the nucleotide sequence of SEQ ID NO: 1, 3, 5, 7 or 9, from which an anti-sense RNA is produced.

At first, the present inventors have discovered from a cotton plant of the genus Gossypium, a gene capable of changing the degree of its expression by treatment with a brassinosteroid. Then, they have obtained several genes which are specifically expressed in a cotton fiber tissue at the stage of fiber elongation, and found that the above cotton plant gene is included in these cotton fiber tissue-specific genes.

The term "gene capable of changing the degree of its expression by treatment with a brassinosteroid" as used herein refers to a gene which is expressed in a plant at a different level when the plant is treated with a brassinosteroid.

The cotton plant of the genus Gossypium include, for example, *Gossypium hirsutum*, *Gossypium barbadense*, *Gossypium arboreum*, *Gossypium anomalum*, *Gossypium armourianum*, *Gossypium klotzchianum* and *Gossypium raimondii*.

The term "brassinosteroid" as used herein refers to various compounds with the different steroid skeletons as depicted below.

The compounds of the first type, such as brassinolide (2α,3α,22R,23R-tetra-hydroxy-24S-methyl-B-homo-7-oxa-5a-cholestan-6-one), dolicholide, homodolicholide, 24-epibrassinolide and 28-norbrassinolide, have a steroid skeleton of the formula:

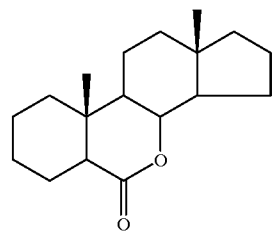

For example, brassinolide is represented by the chemical structural formula:

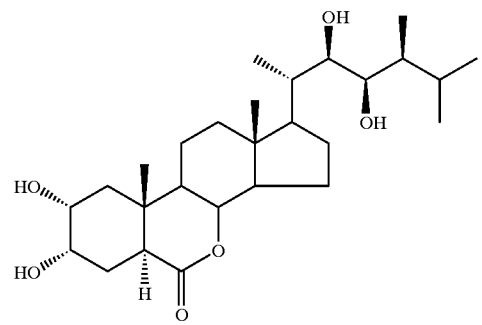

The compounds of the second type, such as castasterone, dolichosterone, homodolichosterone, homocastasterone, 28-norcastasterone, tiffasterol, teasterol, 24-epicastasterone, 2-epicastasterone, 3-epicastasterone, 3,24-diepicastasterone, 25-methyldolichosterone, 2-epi-25-methyldolichosterone and 2,3-diepi-25-methyldolichosterone, have a steroid skeleton of the formula:

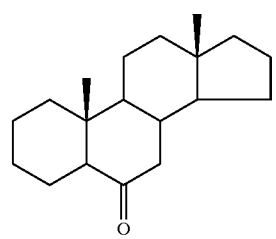

The compounds of the third type, such as 6-deoxocastasterone, 6-deoxodolichosterone and 6-deoxyhomodolichosterone, have a steroid skeleton of the formula:

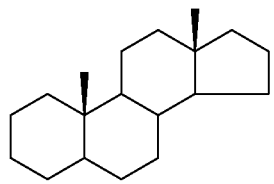

The cotton fiber tissue-specific genes of the present invention can be obtained by an ordinary technique such as differential screening method or differential display method.

The differential screening method is a well-known technique for screening particular clones which are specifically expressed in the desired cell group by utilization of quantitative and qualitative differences in the transcribed products between the desired cell group and the control cell group.

The differential display method is a well-known PCR-utilizing technique for isolating particular genes which are specifically expressed in different cells or under the particular conditions [Liang and Pardee, Science 257, 967 (1992); and Liang et al., Nucleic Acids Research, 21, 3269 (1993)]. The main feature of this method is in that cDNa is synthesized by reverse transcription with 3'-anchored oligo(dT) or random primer and PCR is effected by the use of cDNA as a template with a 10 or 12 mer primer having a random sequence. The PCR products are separated and analyzed by gel electrophoresis. A PCR fragment obtained specifically from a certain cell should be related to an mRNA expressed specifically in that cell.

In the present invention, the differential screening method is used for screening particular clones which are specifically expressed in a cotton fiber tissue at the fiber elongation stage by utilization of quantitative and qualitative differences in the transcribed products between at the fiber elongation stage and at the fiber non-elongation stage.

1. Isolation of Fiber-specific Genes by Differential Screening Method (1) Construction of cDNA Library From the cotton ovules on the 5th day after the flowering, poly(A)$^+$RNA is extracted by the ordinary procedure. Using the isolated poly(A)$^+$RNA as a template, cDNA is synthesized by reverse transcriptase with oligo(dT) primer and then converted into a double-stranded DNA by the polymerase reaction. The double-stranded DNA is inserted into an appropriate vector, which is then used for the transformation of host cells such as *Escherichia coli* to prepare a cDNA library. The poly(A)$^+$RNA isolation and cDNA synthesis may also be carried out by the use of a commercially available cDNA cloning kit. Examples of the vector used for library preparation are λZAPII, λgt10 and λgt11. Examples of the host cell are *E. coli* XL-1 Blue, *E. coli* XL-1 Blue MRF' and *E. coli* SURE.

(2) Screening of Desired Genes From cDNA Library

The desired genes can be obtained by the differential screening method as follows. The phage plaque pattern of the cDNA library prepared by the above method in section 1(1) is replicated onto two filters, each of which is hybridized with either $^{32}$P-labelled cDNA probe prepared by the method as described in section 1(1) from the ovules on the 5th day after the flowering or from the ovules on the 25th day after the flowering. The cDNA corresponding to the desired gene can be selected by detection of a positive hybridization signal only from the cDNA probe prepared from the ovules on the 5th day after the flowering.

The RNA isolation, cDNA preparation, DNA digestion, ligation, transformation, hybridization and other techniques necessary for ordinary gene recombination are as described in the instructional manuals of commercially available enzymes used for the respective procedures or various text books (e.g., Molecular Cloning edited by Maniatis et al., Cold Spring Harbor, 1989, and Current Protocols in Molecular Biology edited by F. M. Ausubel et al., John Wiley & Sons, Inc., 1987).

The nucleotide sequence of the cloned cDNA can be determined by the Maxam-Gilbert method or the dideoxy chain termination method, each of which is carried out by the use of a commercially available kit. The nucleotide sequence may also be automatically determined with an auto-sequencer.

If the cDNA thus analyzed does not correspond to a full-length protein coding sequence, a desired cDNA clone having such a full-length protein coding sequence can be obtained by another plaque hybridization according to the ordinary procedure, or by the RACE (rapid amplification of cDNA ends) technique.

2. Isolation of Fiber-specific Genes by Differential Display Method (1) Isolation of Desired Genes From the fiber tissues of a cotton plant on the 8th day after the flowering, the whole RNA or poly(A)$^+$RNA is extracted by the ordinary procedure. Separately, the whole RNA or poly(A)$^+$RNA is extracted from the fiber-removed ovules (stripped ovules) on the 8th day after the flowering or from the seeds of a cotton plant on the 35th day after the flowering. From the whole RNA or poly(A)$^+$RNA thus extracted, cDNA is synthesized by reverse transcription with anchored oligo(dT) primer (oligo(dT) plus 2 random nucleotides). Using the prepared cDNA as a template, PCR is effected with the same anchored oligo(dT) primer as in the cDNA synthesis and a random primer. The PCR products are separated by gel electrophoresis and examined for the presence of specific bands occurring in the PCR products of the whole RNA or poly(A)$^+$RNA obtained from the fiber tissues of a cotton plant on the 8th day after the flowering, but not in the PCR products from striped ovules. PCR products are ligated into a cloning vector.

To confirm that the genes obtained by the above method are specific both to the fiber elongation stage and to the fiber tissues, Northern hybridization is carried out using the cDNA as a probe with different species of mRNA obtained from other cotton tissues such as stems, leaves, roots and seeds at different stages, and it is determined that these genes are specifically expressed in a fiber tissue at the fiber elongation stage. The genes thus obtained are associated with the elongation of cotton fibers, and the use of such genes for the control of gene expression in a molecular biological manner makes it possible to produce cotton fibers with satisfactory fiber characteristics suitable for their applications.

3. Utilization of Genes Associated with Formation and Elongation of Cotton Fibers The desired genes obtained by the above method in section 1 or 2 can be utilized for mass production of proteins associated with fiber formation and elongation in cotton and other plants. Further, some of the desired genes contain a DNA sequence coding for a signal peptide; therefore, they may be utilized for modification of cell wall components by expression of various proteins in the cell wall, and such a technique can be applied to the breeding of a novel plant having conferred disease resistance or the like.

For example, a gene associated with fiber formation and elongation may be ligated to an appropriate promoter, followed by introduction into cotton or other plants, which makes it possible to increase the content of a desired protein. In contrast, at least one part of the anti-sense strand (I.e., complementary sequence to the coding sequence) of the above gene may be ligated in reverse direction to an appropriate promoter, followed by introduction into a plant and then expression of the so-called anti-sense gene, which makes it possible to decrease the content of a desired protein.

Further, the DNA sequence coding for a signal peptide may be ligated to another gene, followed by introduction into a plant, which makes it possible to allow the gene product to effectively pass through the plasma membrane to the cell wall.

The transformation of plants can be carried out by electroporation in which protoplasts are treated with electric pulses for introduction of plasmids, or by fusion between protoplasts and small cells, cells, lysosomes or the like. Other methods can also be employed, such as microinjection, polyethylene glycol technique or particle gun technique.

With the use of a plant virus as a vector, a desired gene can also be introduced into a plant. A typical example of the plant virus is cauliflower mosaic virus (CaMV). For example, the introduction of a desired gene is carried out as follows. First, a virus genome is inserted in a vector derived from *E. coli* or the like to prepare a recombinant, and a desired gene is inserted in the virus genome. The virus genome thus modified is removed from the recombinant by restriction endonuclease and inoculated into a plant to insert the desired gene into the plant [Hohn et al., Molecular Biology of Plant Tumors, Academic Press, New York, 549–560 (1982), and U.S. Pat. No. 4,407,956].

Further, there is a technique using a Ti plasmid of Agrobacterium. When a plant is infected with bacteria of the genus Agrobacterium, a part of their plasmid DNA is transferred to the plant genome. By making use of such a property, a desired gene can also be introduced into a plant. Upon infection, for example, *Agrobacterium tumefaciens* and *Agrobacterium rhizogenes* induce the formation of crown galls and the formation of hairy roots, respectively. Each of these bacteria has a plasmid designated "Ti-plasmid" or "Ri-plasmid" having T-DNA (transferred DNA) and vir region. The tumor formation is caused by incorporation of T-DNA into the genome of a plant, and then transcription and translation of an oncogene present in the T-DNA in the plant cells. The vir region per se is not transferred to the plant cells, but it is essential to the transfer of T-DNA. Also, the vir region can function even if it is on another plasmid different from the T-DNA containing plasmid [Nature, 303, 179 (1983)].

If a desired DNA is inserted in the T-DNA on the Ti- or Ri-plasmid, the desired DNA can be incorporated into the plant genome upon infection of the plant with these bacteria of the genus Agrobacterium. In this case, a portion inducing the formation of crown galls or hairy roots is removed from the T-DNA of the Ti- or Ri-plasmid without deteriorating the desired transfer function, and the plasmid thus obtained can be used as a vector.

Further, various other vectors can also be used, for example, vectors such as pBI121 (manufactured by Clontech, Co.), which are designated "binary vectors". In this case, the gene associated with fiber formation and elongation is ligated in sense or anti-sense direction to an appropriate promoter, which is then inserted in the binary vector, followed by incorporation into a plant. The binary vectors have no vir region, and the bacteria of the genus Agrobacterium to be used for introduction of these vectors are, therefore, required to contain another plasmid having vir region.

These vectors serve as a shuttle vector which can be amplified not only in the bacteria of the genus Agrobacterium but also in *E. coli*. Accordingly, the recombination of Ti-plasmids can also be carried out with *E. coli*. These vectors have antibiotic-resistance genes, and the screening of transformants can, therefore, be readily done in the transformation of *E. coli*, bacteria of the genus Agrobacterium, plants or the like. These vectors further have 35S promoter of CAMV, and the gene inserted in these vectors can, therefore, be incorporated into the plant genome and then expressed under no regulatory control.

The following will illustrate the introduction of a desired gene by the bacteria of the genus Agrobacterium into a plant and the regeneration of whole plants from the transformed cells in the case of *Arabidopsis thaliana*.

According to the ordinary procedure, seeds of *Arabidopsis thaliana* are sowed in MSO plate (Murashige-Skoog inorganic salts, 4.6 g; sucrose, 10 g; 1000×vitamin stock solution, 1 ml/liter; pH 6.2) and aseptically cultivated. The explants of a root are used to prepare callus cultures on CIM plate (prepared by addition of 2,4-dichlorophenoxyacetic acid and kinetin to MSO plate to yield a final concentration of 0.5 $\mu$g/ml and 0.05 $\mu$g/ml, respectively). A desired gene is ligated to a promoter, which is then inserted in a plasmid having kanamycin-resistance and hygromycin-resistance genes. The bacteria of the genus Agrobacterium transformed with the plasmid are cultured, and the cultures are diluted and dispensed in appropriate portions in tubes. The root explants in callus form are immersed in these tubes and cocultivated on CIM plate for several days. When the bacterial strains are grown enough to be observed by the naked eye, the root explants are sterilized and then cultivated on SIMC plate (prepared by addition of $N^6$-[2-isopentenyl] adenine, indoleacetic acid (IAA) and claforan to MSO plate to yield a final concentration of 5 $\mu$g/ml, 0.15 $\mu$g/ml and 500 $\mu$g/ml, respectively) for several days. These explants are finally cultivated on SIMCS plate (prepared by adding kanamycin and hygromycin B to SIMC plate) with a repeated change to a new plate every week.

The transformed explants are continuously grown, and the appearance of calli will be observed. Because of the screening with antibiotics, the color of non-transformed explants changed to brown. The cultivation is continued until the transformants have a size of about 5 mm to form shoots. When they take the form of complete shoots, the bottom parts of the transformants are cut with a surgical knife so as not to include any callus, and transplanted on RIM plate (prepared by adding IAA to MSO plate to yield a final concentration of 0.5 $\mu$g/ml). If the parts cut from the transformants contain a large callus, the roots, even if produced, have a tendency to spread through the callus, and the vascular bundle may, therefore, be often disconnected between the roots and the shoots. After about 8 to 10 days, these parts are transplanted on a rock wool soaked with inorganic salts medium [5 mM $KNO_3$, 2.5 mM K-phosphate buffer (pH 5.5), 2 mM $MgSO_4$, 2 MM $Ca(NO_3)_2$, 50 $\mu$M Fe-EDTA, 1000×microelements (70 mM $H_3BO_3$, 14 mM $MnCl_2$, 0.5 mM $CuSO_4$, 1 mM $ZnSO_4$, 0.2 mM $Na_2MoO_4$, 10 mM NaCl, 0.01 mM $CoCl_2$) 1 ml/liter].

The plant which has come into flower and then formed siliques is transplanted in the soil soaked with inorganic salts medium, and is grown to give seeds. The seeds are sterilized, sowed in MSH plate (prepared by adding hygromycin B to MSO plate to yield a final concentration of 5 U/ml), and then germinated, thereby obtaining a transformed plant.

From this transformed plant, DNA is extracted according to the ordinary procedure. The DNA is digested with appropriate endonuclease, and subjected to Southern hybridization by the use of the gene associated with fiber formation and elongation as a probe. Thus, it can be confirmed whether transformation has occurred in the plant.

Further, from the transformants or non-transformants, RNA is extracted according to the ordinary procedure, and a probe is prepared which has a sense or anti-sense sequence of the gene associated with fiber formation and elongation. Northern hybridization using these probes makes it possible to examine the degree of expression for the desired gene.

The gene associated with fiber formation and elongation can be expressed specifically in a cotton fiber tissue in the fiber formation process to make a contribution to fiber elongation. Thus, if the nucleotide sequence of this gene is utilized as a marker for the elongation of cotton fibers, the elucidation of fiber elongation mechanism and the isolation of a fiber elongation-controlling gene can be achieved.

With the use of a desired protein necessary for fiber formation and elongation, which also serves as a marker for the formation and elongation of cotton fibers, it becomes possible the establishment of a technique for inducing fiber formation and elongation, the elucidation of fiber formation and elongation mechanism, and the isolation of a fiber formation and elongation-controlling gene. The present invention is, therefore, also quite useful in the technical field of cell formation and elongation.

Further, the nucleotide sequence coding for a protein associated with fiber formation and elongation can be used for gene expression by artificial means such as an in vitro transcription system or with a microorganism such as *E. coli* to give a protein associated with fiber formation and elongation in large quantities and in pure form. Because the protein thus obtained is a protein associated with fiber formation and elongation, it can be used for modifying the structure of plant cell walls and hence can be useful for the processing of plant raw materials used in the industrial field.

It is believed that the gene of the present invention is a key gene associated with the growth stage of plant cells because it is also associated with fiber formation and elongation. Therefore, for example, by the use of cauliflower mosaic virus (CaMV) 35S promoter, all the organs of a plant can be brought into form change over the whole stage of its life cycle. The use of a regulatory promoter for light, heat or wounding makes it possible to prepare a plant capable of changing its form depending upon the growth environment. Further, by the use of an organ- or tissue-specific promoter, a form change can be caused only in particular organs or tissues. For example, a promoter capable of causing transcription only at the time of fiber formation can be used for controlling the formation of fibers and causing a modification of fiber characteristics.

According to the present invention, an improvement can be attained in the characteristics (e.g., fiber length, fiber fineness, fiber strength) and yield of cotton fibers. The gene of the present invention can be used to prepare a novel variety of cotton plant having a genetically fixed character of producing cotton fibers with improved fiber characteristics in high yield.

The present invention will be further illustrated by the following Examples, which are not to be construed to limit the scope of the invention.

EXAMPLE 1

Cloning of Genes Associated With Cotton Fiber Formation by Differential Screening Method 1. Preparation of Poly(A)$^+$RNA The cotton plant, Supima (*Gossypium barbadense*), cultivated in a field was used as the test material. The ovules on the 5th day after the flowering and those on the 25th day after the flowering as a control sample were collected, and about 5 g of each of the ovules thus obtained was immediately frozen in liquid nitrogen and pulverized with a mortar in the presence of liquid nitrogen. To the pulverized ovules was added 10 ml of 0.2 M Tris-acetate buffer for extraction [containing 5 M guanidinethiocyanate, 0.7% β-mercaptoethanol, 1% polyvinylpyrrolidone (M.W., 360, 000) and 0.62% sodium N-lauroylsarcosinate, pH 8.5], and the mixture was further pulverized with a polytron homogenizer (manufactured by KINEMATICA Co.) under ice cooling for 2 minutes. At that time, β-mercaptoethanol and polyvinylpyrrolidone were added to the buffer just before use. The pulverized mixture was centrifuged at 17,000×g for 20 minutes, and the supernatant was collected.

The supernatant was filtered through a miracloth, and the filtrate was gently overlaid on 1.5 ml of 5.7 M aqueous cesium chloride solution in a centrifuge tube, followed by centrifugation at 155,000×g for 20 hours at 20° C. The supernatant was discarded, and the precipitated RNA was collected. The precipitate was dissolved in 3 ml of 10 mM Tris-HCl and 1 mM EDTA-2Na, pH 8.0 (referred to as TE buffer), to which a mixture of phenol, chloroform and isoamyl alcohol (volume ratio, 25:24:1) was added at the same volume. The mixture was well agitated and then centrifuged at 17,000×g for 20 minutes, and the upper aqueous layer was collected. To the aqueous layer obtained were added a 0.1-fold volume of 3 M aqueous sodium acetate solution (adjusted to pH 6.2 by addition of gracious acetic acid) and a 2.5-fold volume of ethanol. The mixture was well agitated and allowed to stand without disturbance at −20° C. overnight. The mixture was then centrifuged at 17,000×g for 20 minutes, and the precipitate was washed with 70% ethanol and dried in vacuo.

The dry product was dissolved in 500 μl of TE buffer to give a solution of the whole RNA. This RNA solution was incubated at 65° C. for 5 minutes and then immediately cooled on ice, to which 2×coupling buffer (10 mM Tris-HCl, 5 mM EDTA-2Na, 1M NaCl, 0.5% SDS, pH 7.5) was added at the same volume. The mixture was overlaid on an oligo-dT cellulose column (manufactured by Clontech, Co.) which had been previously equilibrated with equilibration buffer (10 mM Tris-HCl, 5 mM EDTA-2Na, 0.5 M NaCl, 0.5% SDS, pH 7.5). The column was then washed with an about 10-fold volume of the equilibration buffer, and the poly(A)$^+$RNA was eluted with elution buffer (10 mM Tris-HCl, 5 mM EDTA-2Na, pH 7.5).

To the eluate obtained were added a 0.1-fold volume of the 3M aqueous sodium acetate solution and a 2.5-fold volume of ethanol, and the mixture was allowed to stand without disturbance at −70° C. The mixture was then centrifuged at 10,000×g, and the precipitate was washed with 70% ethanol and dried in vacuo. The dry product was dissolved again in 500 μl of TE buffer, and purification was repeated with an oligo-dT cellulose column. The poly(A)$^+$RNA obtained from the ovules on the 5th day after the flowering was used for preparation of a cDNA library and a cDNA probe for differential screening, and the poly(A)$^+$RNA obtained from the ovules on the 25th day after the flowering was used for preparation of a cDNA probe for differential screening.

2. Preparation of cDNA Library at Fiber Elongation Stage

A cDNA library was prepared with ZAP-cDNA Synthesis Kit (manufactured by Stratagene Co.). The poly(A)+RNA obtained from the ovules on the 5th day after the flowering in section 1 was used as a template, and double-stranded cDNA was synthesized by reverse transcriptase with oligo (dT) primer according to the method of Gubler and Hoffman et al. [Gene, 25, 263–269 (1983)].

To both ends of the cDNA obtained were ligated EcoRI adaptors (each having XhoI and SpeI sites in the inside), and the ligated DNA was digested with XhoI. The fragment was then ligated between the EcoRI and XhoI sites of the λ phage vector, λZAPII arm, and the vector was packaged with an in vitro packaging kit (manufactured by Stratagene Co., GIGAPACK Gold), followed by infection into *E. coli* strain SURE ($OD_{660}$=0.5), which afforded a number of recombinant λ phages serving as the cDNA library specific to the fiber elongation stage. This cDNA library had a size of $5.0 \times 10^6$.

3. Preparation of Probes

The poly(A)+RNA prepared from the ovules on the 5th day after the flowering or on the 25th day after the flowering was used as a template, cDNA was synthesized by reverse transcriptase M-MLV (manufactured by Toyobo Co., Ltd.) with oligo(dT) primer. After the synthesis, alkali treatment was carried out to remove the poly(A)+RNA by hydrolysis. The cDNA thus obtained was used as a template, and a $^{32}$P-labelled probe was prepared with Random Primed DNA Labeling Kit (manufactured by USB Co.).

The $^{32}$P-labelled probes thus prepared by the cDNA on the 5th day after the flowering and by the cDNA on the 25th day after the flowering were used as a probe for the fiber elongation stage and as a probe for the fiber non-elongation stage, respectively, for differential screening.

4. Screening of Genes Associated With Fiber Formation and Elongation

The above λ phages constituting the cDNA library from the ovules at the fiber elongation stage were infected into *E. coli* cells, which were grown on LB agar medium. About 50,000 plaques of λ phage DNA were replicated on two nylon membranes (Hybond-N, manufactured by Amersham Corp.).

The nylon membranes having replicated λ phage DNA thereon were transferred on a filter paper containing a solution for alkali denaturation (0.5 M NaOH, 1.5 M NaCl) and then allowed to stand for 4 minutes. The nylon membranes were transferred on a filter paper containing a solution for neutralization (0.5 M Tris-HCl, 1.5 M NaCl, pH 8.0) and then allowed to stand for 5 minutes. After washing with 2×SSC (0.3 M NaCl, 0.03 M trisodium citrate), these membranes were subjected to DNA fixation with Stratalinker (manufactured by Stratagene Co.). The membranes thus treated for DNA fixation were prehybridized in hybridization buffer [50% formamide, 0.5% SDS, 6×SSPE (3M NaCl, 0.2 M $NaH_2PO_4$, 20 mM EDTA-2Na, pH 7.4), 5×Denhardt solution (0.1% Ficoll, 0.1% polyvinylpyrrolidone, 0.1% bovine serum albumin), 50 µg/ml denatured salmon sperm DNA] at 42° C. for 3 hours, and the cDNA probes (for the fiber elongation stage and for the fiber non-elongation stage) prepared in section 3 were separately added to the respective membranes, followed by hybridization at 42° C. for 20 hours. Thereafter, the membranes were removed and washed with solutions each containing 2×SSC, 1×SSC, 0.5×SSC or 0.1×SSC at 42° C. for 1 to 2 hours. These membranes were dried and then exposed overnight to X-ray films by allowing to closely adhere thereto.

As a result, 34 positive clones capable of hybridizing more strongly with the probe for the fiber elongation stage than with the probe for the fiber non-elongation stage were selected. The analysis was carried out for three colones having particularly strong hybridization signals, which were designated KC18, KC22 and KC03, respectively.

From the phage DNA of KC18, KC22 or KC03, plasmid clone pK18, pKC22 or pKC03 each having a cDNA insert was prepared, respectively, by the in vivo excision method with ZAP-cDNA Synthesis Kit (manufactured by Stratagene Co.).

First, 200 µl of each clone-containing phage solution was mixed with 200 µl of *E. coli* XL1-Blue suspension and 1 µl of helper phage R408 suspension, and the mixture was incubated at 37° C. for 15 minutes, to which 3 ml of 2×YT medium was added. Shaken cultures were grown at 37° C. for 2 hours and then treated at 70° C. for 20 minutes, followed by centrifugation at 4000×g for 10 minutes, and the supernatant was collected. Then, 30 µl of the supernatant was mixed with 30 µl of *E. coli* SURE suspension, and the mixture was incubated at 37° C. for 15 minutes and then inoculated on several microliters of LB agar medium containing 50 ppm ampicillin, followed by incubation at 37° C. overnight. The colony-forming *E. coli* contained the plasmid clone pKC18, pKC22 or pKC03 each having the cDNA insert.

The nucleotide sequences of the cDNA inserts in these plasmids were determined by the dideoxy chain termination method [Messing, Methods in Enzymol., 101, 20–78 (1983)]. The nucleotide sequences are shown in the Sequence Listing, SEQ ID NOs: 1 (clone KC18), 3 (clone KC22) and 5 (clone KC03), and the deduced amino acid sequences in the Sequence Listing, SEQ ID NOs: 2, 4 and 6, respectively. These sequences correspond to the cDNA nucleotide sequence and amino acid sequence, respectively, of a gene exhibiting an increased degree of its expression in a fiber tissue-specific manner at the fiber elongation stage.

The search regarding the homology in nucleic acid sequence of these genes to known genes in the data base revealed that KC03 has homology to the extensin gene of tomato and KC22 has partial homology to the xyloglucantransferase of red bean, tomato or the like [Nishitani et al., J. Biol. Chem., 268, 25364–25368 (1993)] and the meri-5 gene which is specifically expressed in an apical meristem of Arabidopsis [Medford, J. I., Elmer, J. S., and Klee, H. J., Plant Cell, 3, 359–370 (1990)]. With respect to KC18, no homology was found to known genes.

5. Northern Blot Analysis

To confirm that these genes are expressed in a fiber tissue-specific manner at the fiber elongation stage, Northern blotting was carried out as described below.

From the seeds, leaves, seedlings and intact ovules on the 10th day after the flowering, cotton fibers and fiber-removed ovules (stripped ovules) on the 14th day after the flowering, and fiber-removed ovules (stripped ovules) on the 22nd day after the flowering of Supima (*Gossypium barbadense*), RNA was extracted in the same manner as described in section 1. Then, 20 µg of the whole RNA obtained was subjected to 1.5% formaldehyde agarose gel electrophoresis, followed by overnight blotting on a nylon membrane (Hybond-N, manufactured by Amersham Corp.). The membrane was subjected to RNA fixation with UV crosslinker, and then prehybridized in a prehybridization buffer [50% formamide, 5×Denhardt solution, 0.1% SDS, 10 µg/ml salmon sperm DNA, pH 7.0] at 42° C. for 6 hours. The full-length cDNA of KC18, KC22 or KC03 was used as a template, and a probe was prepared with $^{32}$P-dCTP and Random Labeling Kit (manufactured by Amersham Corp.) for each gene. This probe was added to the prehybrization solution, followed by overnight hybridization at 42° C. After the hybridization, the membrane was washed twice with a washing solution containing 1×SSC and 0.1% SDS at 60° C. for 30 minutes. Then, autoradiograms were prepared by exposing the membrane to an X-ray film (manufactured by Eastman Kodak Co.).

In the case of KC18, specific signals were obtained from the intact ovules on the 10th day after the flowering were obtained, as shown in FIG. 1. Signals were also obtained from the cotton fibers at the fiber elongation stage (cotton fibers on the 14th day). In contrast, almost no signals were obtained from the leaves, seeds and seedlings. This probably indicates that KC18 is highly expressed in the cotton fibers at the fiber elongation stage.

Figure 2:
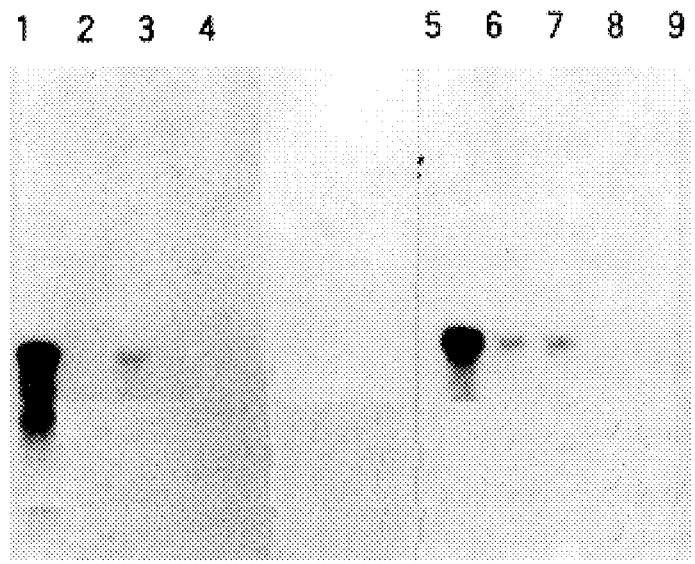
FIG. 2 is a photograph showing the results of Northern blotting of KC22. The tissue specificity of KC22 gene expression was revealed; lane 1, intact ovule on the 10th day after the flowering; lane 2, mature seed; lane 3, seedling after 18 days; lane 4, leaf; lane 5, intact ovule on the 10th day after the flowering; lane 6, fiber on the 14th day after the flowering; lane 7, stripped ovule on the 14th day after the flowering; lane 8, fiber on the 22nd day after the flowering; and lane 9, stripped ovule on the 22nd day after the flowering.

In the case of KC22, strong signals were obtained from the intact ovules on the 10th day from the flowering, and signals were also obtained from the cotton fibers and stripped ovules on the 14th day after the flowering and from the cotton fibers on the 22nd day after the flowering, as shown in FIG. 2. The seedlings gave slight signals, whereas the seeds and leaves gave no signals. This probably indicates that KC22 is highly expressed in the cotton fibers at the fiber elongation stage, particularly in the intact ovules on the 10th day after the flowering.

Figure 3:
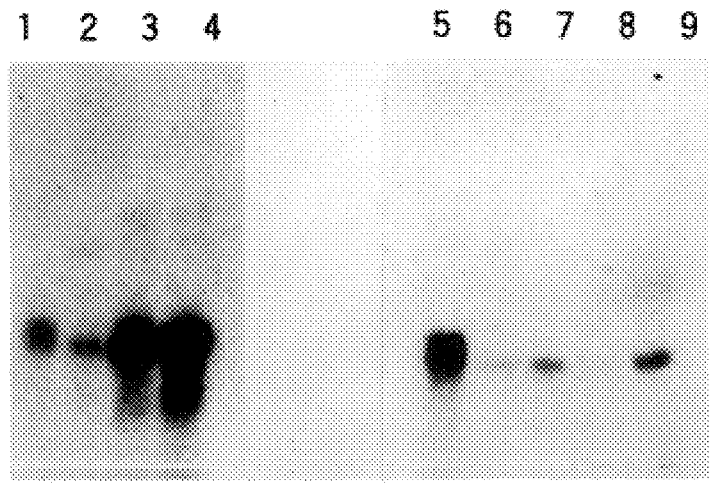
FIG. 3 is a photograph showing the results of Northern blotting of KC03. The tissue specificity of KC03 gene expression was revealed; lane 1, intact ovule on the 10th day after the flowering; lane 2, mature seed; lane 3, seedling after 18 days; lane 4, leaf; lane 5, intact ovule on the 10th day after the flowering; lane 6, fiber on the 14th day after the flowering; lane 7, stripped ovule on the 14th day after the flowering; lane 8, fiber on the 22nd day after the flowering; and lane 9, stripped ovule on the 22nd day after the flowering.

In the case of KC03, strong signals were obtained in the ovules on the 10th day after the flowering, as shown in FIG. 3.

6. Expression of Desired Gene in E. coli

The transformants obtained above (in the case of KC18) were suspended in 50 ml of LB medium containing 100 μg/ml of ampicillin, and shaken cultures were grown at 37° C. When the turbidity $OD_{660}$ of the shaken cultures became 0.2, isopropyl-β-D-thiogalactopyrenosido (IPTG) was added to yield a final concentration of 10 mM. The shake cultures were further grown at 37° C. until the turbidity $OD_{660}$ became 1.0. After completion of the culturing, bacterial cells were collected by centrifugation at 1600×g for 15 minutes. The collected bacterial cells were suspended in a 4-fold volume of lysis buffer [50 mM Tris-HCl (pH 8.0), 1 mM EDTA-2Na, 1 μM PMSF (phenylmethylsulfonyl fluoride), 10% sucrose], to which Lysozyme (manufactured by Sigma Co.) was added to yield a final concentration of 1 mg/ml, followed by allowing to stand on ice without disturbance for 10 minutes. After 10 minutes, non-ionic surfactant Nonidet P-40 (manufactured by Sigma Co.) was added to the cell suspension to yield a final concentration of 1%, and the mixture was further allowed to stand on ice without disturbance for 10 minutes, followed by centrifugation at 48,000×g for 1 hour. To the supernatant obtained was added 2×Laemli sample buffer [0.125 M Tris-HCl (pH 6.8), 20% glycerol, 10% β-mercaptoethanol, 6% SDS, 0.1% bromophenol blue] at the same volume, and the mixture was boiled for 2 minutes, followed by SDS-polyacrylamide gel electrophoresis (SDS-PAGE). After completion of the electrophoresis, the gel was stained with Coomassie brilliant blue (CBB) and decolorized with 7% acetic acid and 25% methanol. A band was observed near the position corresponding to the molecular weight of 41 kDa as desired, and the expression of the desired gene was thus confirmed.

7. Preparation of Arabidopsis thaliana Transformant (1) Construction of Plasmid

The nucleotide sequence of KCl 8 as shown by SEQ ID NO: 1 was digested with PstI and HindIII so as to contain the whole open reading frame thereof, and treated with S1 nuclease in order to produce blunt-ends. This fragment was subcloned in binary vector pBI101-Hm2 having a blunt-ended 35S promoter ligated thereto. The plasmid thus obtained was designated pBI35S-18. The transformed E. coli JM109 was designated E. coli JM109/pBI35S-18.

(2) Introduction of Plasmid into Agrobacterium

The E. coli pBI35S-18(+) obtained in section 7(1) and the E. coli strain HB101 containing helper plasmid pRK2013 were separately cultured on LB medium containing 50 mg/l of kanamycin at 37° C. overnight, while the Agrobacterium strain EHA101 was cultured on LB medium containing 50 mg/l of kanamycin at 37° C. over two successive nights. Then, bacterial cells were harvested by taking 1.5 ml of each of the cultures in an Eppendorf tube, and then washed with LB medium. These bacterial cells were suspended in 1 ml of LB medium, after which three kinds of bacteria were mixed together in 100 μl portions. The mixture was plated on LB agar medium and incubated at 28° C. for ensuring the conjugation transfer of plasmids to Agrobacterium. After 1 to 2 days, a part of the medium was scratched by means of a sterile loop, and spread over LB agar medium containing 50 mg/l kanamycin, 20 mg/l hygromycin B and 25 mg/l chloramphenicol. The incubation was continued at 28° C. for 2 days, and a single colony was selected. The transformant thus obtained was designated EHA101/pBI35S-18.

(3) Cultivation of Sterile Arabidopsis thaliana

Several dozens of seeds of Arabidopsis thaliana stain Wassilewskija (hereinafter referred to as strain WS; furnished by Dr. Shinmyo in Osaka University) were placed in a 1.5-ml tube, to which 1 ml of 70% ethanol was added, and the seeds were allowed to stand for 3 minutes. The seeds were immersed in a solution for sterilization (5% sodium hypochlorite, 0.02% Triton X-100) for 3 minutes, washed five times with sterile water, and then sowed in MSO plate (4.6 g of Murashige-Skoog inorganic salts, 10 g of sucrose, 1 ml/liter 1000×vitamin stock solution, pH 6.2). This plate was allowed to stand at 4° C. for 2 days for low-temperature treatment and then cultivated at 22° C. in a plant incubator (model MLR-350HT, manufactured by Sanyo Electric Co., Ltd.) under long-day conditions (16 hours light and 8 hours dark) at a light intensity of 6000 lux for 10 days.

(4) Infection with Agrobacterium

The roots of several pieces of the above strain WS cultivated for 10 days in section 7(3) were gathered together, cut with a surgical knife to have a uniform length of about 1.5 to 2.0 cm, and placed in order on CIM plate (prepared by adding 2,4-dichlorophenoxyacetic acid and kinetin to MSO plate to yield a final concentration of 0.5 μg/ml and 0.05 μg/ml, respectively). These root explants were cultivated under long-day conditions (16 hours light and 8 hours dark) at a light intensity of 3000 lux for 2 days. MS diluent (6.4 g/liter Murashige-Skoog inorganic salts, pH 6.3) was 3-fold diluted and dispensed in 1 ml portions into tubes, in which the roots in callus form were immersed for 10 minutes. These explants were placed in order on two layers of sterile filter papers to remove excess water, transferred on fresh CIM plate, and cocultivated for 2 days under the same conditions as described above.

(5) Sterilization

The explants grown to a degree enough to observe the respective bacterial strains with the naked eye were placed in a solution for sterilization (prepared by adding claforan to MS diluent to yield a final concentration of 200 μg/ml), followed by washing with gentle shaking for 60 minutes. After five repetitions of this procedure, these explants were placed on a sterile filter paper to remove water, placed in order on SIMC plate (prepared by adding $N^6$-[2-isopentenyl] adenine, IAA and claforan to MSO plate to yield of a final concentration of 5 µg/ml, 0.15 µg/ml and 500 µg/ml, respectively), and cultivated under long-day conditions (16 hours light and 8 hours dark) at a light intensity of 6000 lux for 2 days.

(6) Selection of Transformed Plants

The above explants cultivated for 2 days in section 7(5) were transplanted on SIMCS plate (prepared by adding hygromycin B to SIMC plate to yield a final concentration of 4.6 U/ml) and cultivated tinder long-day conditions (16 hours light and 8 hours dark) at a light intensity of 6000 lux. Thereafter, these explants were transplanted on fresh SIMCS plate every week. The transformed explants were continuously grown to become dome-shaped swollen calli, while the color of non-transformants changed to brown. The calli of the transformants exhibited green color after about 2 weeks. After about 1 month, shoots were formed.

(7) Regeneration of Transformed Plants

Shoots were cut with a razor or a surgical knife so as not to include any callus, and slightly inserted into RIM plate as if they were placed thereon. After 8 to 10 days, the plant having several roots of about 1 to 2 cm in length was transplanted with a pincette in a mini-pot of rock wool (manufactured by NITTO BOSEKI CO., LTD) soaked with inorganic salts medium [5 mM $KNO_3$, 2.5 mM K-phosphate buffer (pH 5.5), 2 mM $MgSO_4$, 2 mM $Ca(NO_3)_2$, 50 µM Fe-EDTA, 1000×microelements (70 mM $H_3BO_3$, 14 mM $MnCl_2$, 0.5 mM $CuSO_4$, 1 mM $ZnSO_4$, 0.2 mM $Na_2MoO_4$, 10 mM NaCl, 0.01 mM $CoCl_2$) 1 ml/liter], and cultivated. After flowering and podding, these plants were transplanted in the soil which was prepared by mixing pearlite and vermiculite (manufactured by TES Co.) at a ratio of 1:1 and soaking in inorganic salts medium. After about 1 month, a few hundred of seeds per plant were obtained. These seeds are hereinafter referred to as T1 seeds.

(8) Selection of Antibiotic-resistant Strains

About one hundred T1 seeds were sterilized by the same method as described in section 7(3), and then sowed in MSH plate. Hygromycin B-resistant strains were germinated at a ratio of approximately 3:1.

(9) DNA Extraction and Southern Hybridization

The T1 seeds germinated in section 7(8) were transplanted with a pincette in a mini-pot of rock wool soaked with inorganic salts medium, and cultivated at 22° C. under long-day conditions (16 hours light and 8 hours dark) at a light intensity of 6000 lux. After 2 weeks, the aerial parts of the plants were cut with a surgical knife as if the surface of the rock wool was smoothed with a knife, and immediately frozen with liquid nitrogen. The frozen aerial parts were finely pulverized with a mortar in the presence of liquid nitrogen, to which 3 ml of DNA extraction buffer [200 mM Tris-HCl (pH 8.0), 100 mM EDTA-2Na, 1% sodium N-lauroylsarcosinate, 100 µg/ml proteinase K] was added, and the mixture was well agitated and then incubated at 60° C. for 1 hour, followed by centrifugation at 10,000×g for 10 minutes. The supernatant was filtered through a miracloth, and the filtrate was transferred in a new tube. After three extractions with a mixture of phenol, chloroform and isoamyl alcohol (25:24:1), ethanol precipitation was carried out. The precipitate was dissolved in TE buffer. From about 2.0 g of the plants, 20 µg of genomic DNA was obtained. Each 1 µg of genomic DNA was digested with EcoRI and HindIII, and the DNA fragments were subjected to 1% agarose electrophoresis and Southern hybridization.

In the same manner as described, the non-transformed seeds of the WS strain were germinated and grown, after which DNA isolated from the plants was digested with PstI, and the DNA fragments were subjected to 1% agarose gel electrophoresis and Southern hybridization. As the probe for hybridization, pKC18 was used.

Southern hybridization was carried out according to the method described in Molecular Cloning, A Laboratory Manual, ch. 9, pp. 31–58 (Cold Spring Harbor, 1989). That is, each DNA sample was subjected to 1% agarose gel electrophoresis, followed by alkali denaturation and overnight Southern blotting on a nylon membrane (Hybond-N, manufactured by Amersham Corp.). The membrane was irradiated with an UV trans-illuminator (254 nm) for 3 minutes to cause DNA fixation. This membrane was prehybridized in 5 ml of prehybridization buffer [5×Denhardt solution, 6×SSC, 0.1% SDS, 10 µg/ml salmon sperm DNA] at 50° C. for 2 hours, followed by hybridization with a probe at 50° C. overnight. The membrane was washed twice with a washing solution containing 2×SSC and 0.1% SDS at room temperature for 10 minutes and then twice with the same solution at 50° C. for 30 minutes. After the membrane was dried, autoradiograms were prepared by exposing the membrane to an X-ray film (manufactured by Eastman Kodak Co.) in a cassette to at −80° C. overnight. Comparison of signal patterns detected by Southern hybridization was made among: (i) the non-transformants; (ii) the transformants having pKC18; and (iii) the transformants having only the vector.

Specific signals from the transformants (ii) were observed at positions of about 1.6 and 0.7 kbp for the PstI-digested sample and at a position of about 3.0 kbp for the HindIII-digested sample, in addition to endogenous signals common to (i), (ii) and (iii), indicating that the desired gene was incorporated in the transformants (ii).

EXAMPLE 2

Gene Isolation From RT-PCR Products by Differential Display Method

1. Preparation of poly(A)$^+$RNA

The cotton plant, Coker 312 (*Gossypium hirstum*), cultivated in a field was used as the test material. In the same manner as described in Example 1, section 1, the whole RNA was prepared from the cotton fibers or from the fiber-removed ovules (stripped ovules) on the 8th day after the flowering.

2. DNase Treatment

In a 1.5 ml microtube was placed 30–50 µg of the whole RNA, to which 40 µl of DNase reaction buffer, 5 µl of RNase inhibitor and 10 µl of DNase I were added, and the volume was adjusted to 100 µl by addition of diethylpyrocarbobate-treated water. The mixture was incubated at 37° C. for 30 minutes, and the whole RNA was purified by phenol extraction. To the purified whole RNA were added a 0.5-fold volume of 7.5 M aqueous ammonium acetate solution and a 2-fold volume of ethanol, and the mixture was well agitated and then allowed to stand at −20° C. without disturbance for 1 hour. The mixture was centrifuged at 10,000×g for 15 minutes, and the resulting precipitate was washed with 70% ethanol and dried in vacuo.

3. Synthesis of First-Strand cDNA

In a 0.5 ml microtube was placed 2 µg of the DNase-treated whole RNA, and the volume was adjusted to 25 µl by addition of diethylpyrocarbonate-treated water. The mixture was heat treated at 65° C. for 10 minutes and then immediately cooled on ice. The first-strand cDNA was synthesized by reverse transcriptase M-MLV (manufactured by Toyobo Co., Ltd.) with oligo(dT) primer having two additional nucleotides M and N (wherein M is A, C or G and N is A, C, G or T) on the 3' end thereof.

4. PCR Amplification

The first-strand cDNA obtained in section 3 was subjected to PCR with the oligo(dT) primer used for the cDNA synthesis and random decamer primer. The steps of PCR at 94° C. for 30 seconds, at 42° C. for 1 minute and at 72° C. for 30 seconds were repeated in 40 cycles, and finally the reaction was effected at 72° C. for 5 minutes.

5. DNA Sequence Gel Electrophoresis

Figure 4:
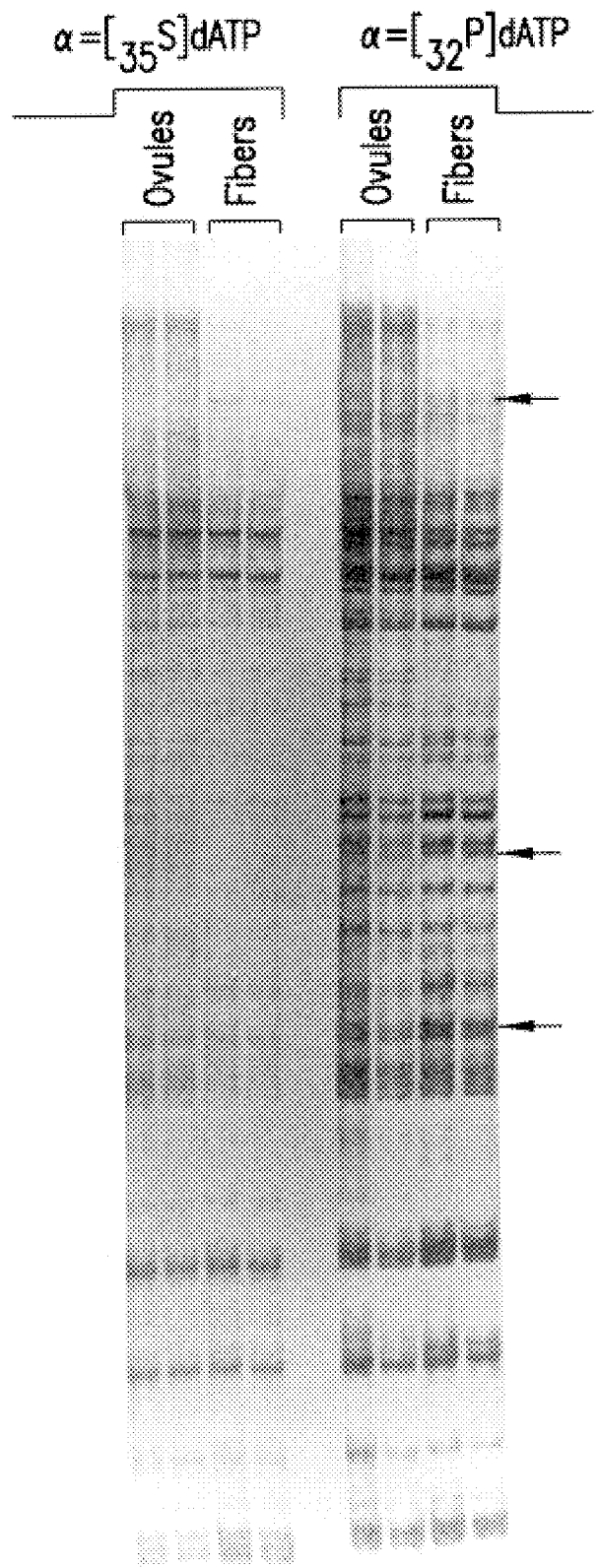
FIG. 4 is a photograph showing the differential display bands on 6% denaturing DNA sequence gel for the whole RNA from the stripped ovules or fibers on the 8th day after the flowering; upper four lanes, $^{35}$S-labelled samples; and lower four lanes, $^{32}$P-labelled samples. In this photograph, three arrows point to fiber-specific bands.

The PCR amplified products were subjected to 6% denatured polyacrylamide sequence gel electrophoresis. After completion of the electrophoresis, the gel was dried, and autoradiograms were prepared by exposing the dried gel to an X-ray film (manufactured by Eastman Kodak, Co.) in a cassette at −80° C. for 10 hours. The results are shown in FIG. 4.

6. Identification and Collection of Specific PCR Products

Twenty desired bands detected only in the fiber tissue were confirmed and removed from the gel with a blade in the razor. The removed gel portions were placed in a 1.5 ml microtube, to which 300 μl of water was added, and the mixture was boiled for 10 minutes, so that the DNA fragments were separated from the gel portions. The separated twenty DNA fragments were subcloned in the TA cloning vector (manufactured by Invitrogen, Co.) and then transformed into *E. coli*, followed by preparation of plasmid DNA according the ordinary procedure. The nucleotide sequence of plasmid DNA was determined by the dideoxy chain termination method [Messing, Methods in Enzymol., 101, 20–78 (1983)].

The clone having no start (ATG) codon on the 5' end thereof was screened from the fiber tissue-derived cDNA library by the PCR method.

7. Northern Blot Analysis

The cotton plant, Coker 312 (*Gossypium hirstum*) was used as the test material. In the same manner as described in Example 1, section 5, northern hybridization analysis was carried out for tissue-specificity and stage-specificity with two clones (Gh2 and Gh3) obtained by the differential display method as probes.

Figure 5:
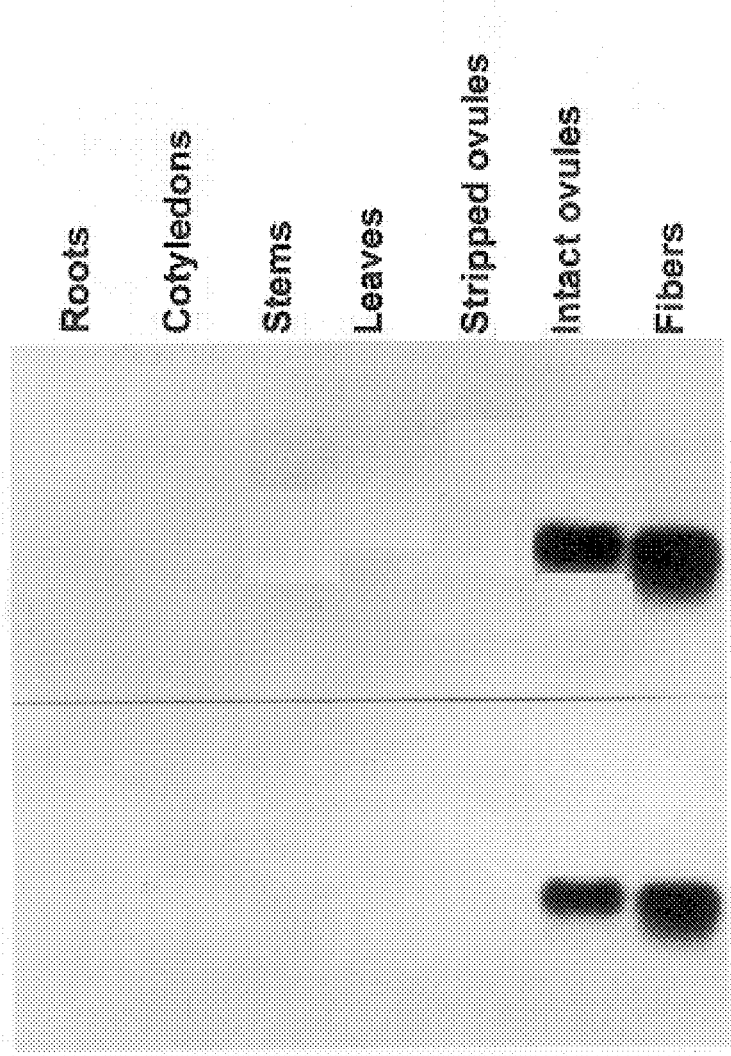
FIG. 5 is a photograph showing the results of Northern blotting of Gh2 on different cotton tissues, i.e., root, cotyledon, stem, leaf, stripped ovule, intact ovule and fiber.
Figure 6:
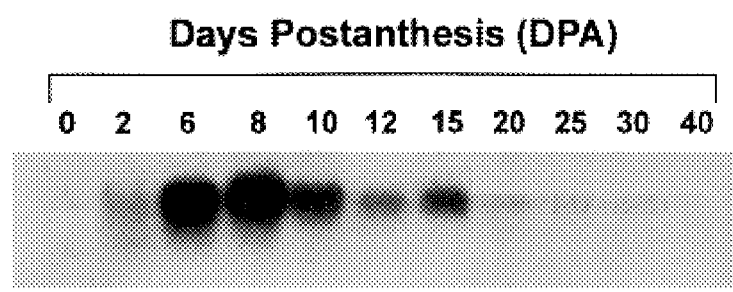
FIG. 6 is a photograph showing the results of Northern blotting of Gh2 at different fiber development stages, i.e., from the flowering day to the 40th day after the flowering.

As a result, Gh2 gave strong hybridization signals for the cotton fibers and intact ovules on the 8th day after the flowering, as shown in FIG. 5. Further, it was examined what stage in the fiber growth process Gh2 was specifically expressed, and it was found that Gh2 gave strong hybridization signals for the cotton fibers on the 6th day, 8th day, 10th day, 12th day and 15th day after the flowering, which are in the fiber elongation stage, as shown in FIG. 6. Thus, it was revealed that Gh2 is highly expressed in a cotton fiber tissue at the fiber elongation stage.

Figure 7:
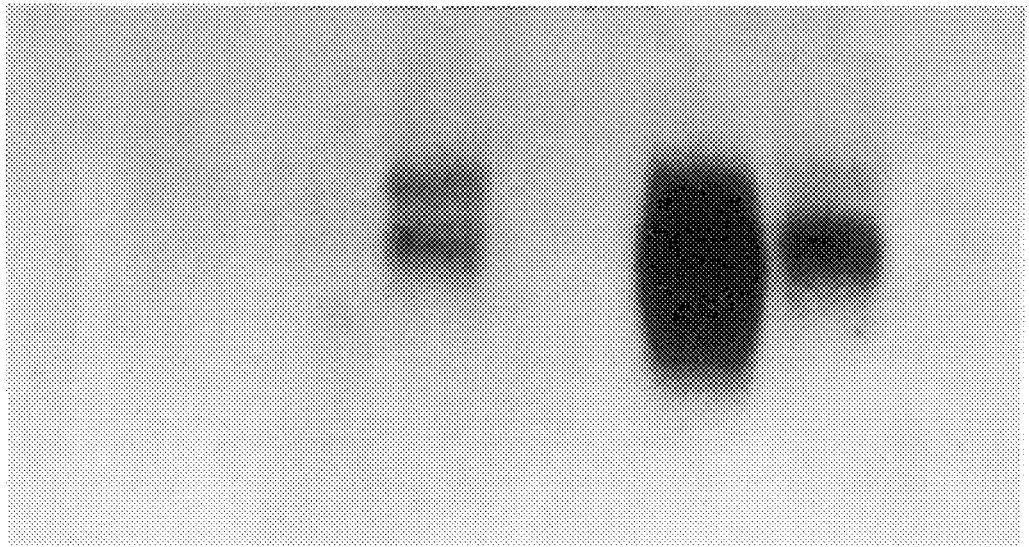
FIG. 7 is a photograph showing the results of Northern blotting of Gh3 on different cotton tissues, i.e., root, stem, leaf, petal, fiber, intact ovule and stripped ovule.
Figure 8:
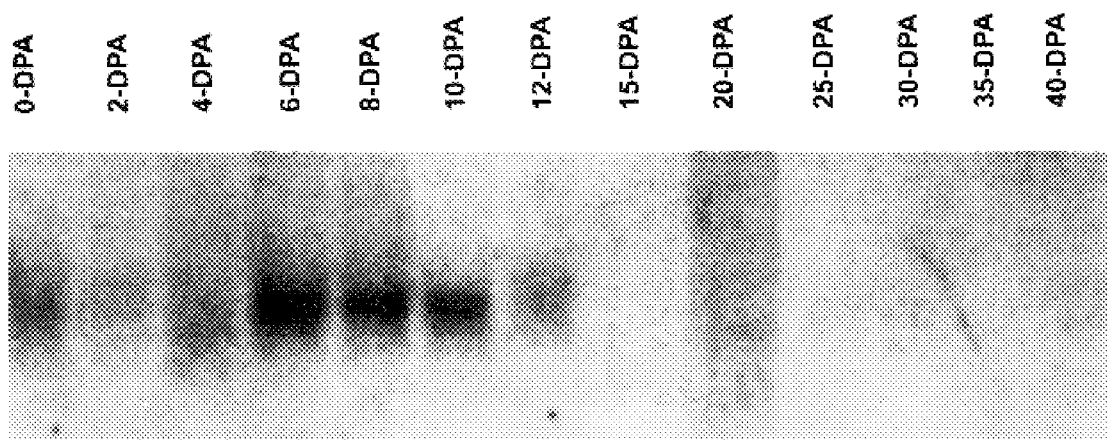
FIG. 8 is a photograph showing the results of Northern blotting of Gh3 at different fiber development stages, i.e., from the flowering day to the 40th day after the flowering.

On the other hand, Gh3 gave slight hybridization signals for the petals and strong hybridization signals for the cotton fibers and intact ovules on the 8th day after the flowering, as shown in FIG. 7. Further, Gh3 was examined for stage-specificity, and it was found that Gh2 gave strong hybridization signals for the cotton fibers on the 6th day, 8th day and 10th day after the flowering, which are in the fiber elongation stage, as shown in FIG. 8. Thus, it was revealed that Gh3 is highly expressed in a cotton fiber tissue at the fiber elongation stage.

8. Search of Homology to Known Genes

With respect to Gh2 and Gh3 genes, the search of homology to known genes in the nucleotide sequence data base was carried out. Gh2 gene exhibited a high degree of homology to a nucleotide sequence coding for the cotton fiber ACP (acyl carrier protein). The comparison of amino acid sequences revealed that the amino acid sequence encoded in Gh2 gene has 58–67% homology to other plant ACPs, as shown in Table 1 below. Twelve highly-conserved amino acids around the site of binding to a prosthetic group, which site is known as a serine residue, are the same as those found in all the plants' ACPs. The nucleotide sequence coding for the cotton ACP has approximately the same degree of similarity both to the nucleotide sequences of monocotyledonous and dicotyledonous plants. The precursor of a certain plant ACP contains at the cleavage site between the transpeptide and the mature ACP protein, and the sequence around this site is conserved. It is believed that Gh2 gene codes for the cotton fiber tissue-specific ACP. The cDNA of the cotton fiber tissue-specific ACP has a sequence of CC|AAK (wherein base symbols "C", "A" and "K" mean cytosine, adenine, guanine or thymine/uridine, respectively, and "I" means a cleavage site), which is very similar to that of barley's ACP III. The epidermal cells of ovules begin elongation after the flowering. The fibers elongate from just after the flowering to the 25th day after the flowering, and then stimulate the secondary cell wall thickening, resulting in a maturation at the final stage. The mature cotton fibers are single cells each having a final diameter of 20–40 μm and a length of 20–40 mm. Such an elongation corresponds to a 1000- to 3000-fold increase in length, during which Gh2 gene seems to be highly expressed and associated with the fiber elongation. In particular, the expression of Gh2 gene is controlled in a cotton fiber tissue-specific manner, and it is, therefore, believed that Gh2 gene is specifically expressed in a cotton fiber tissue at the fiber elongation stage in order to respond to a great demand for lipid synthesis necessary in the fiber elongation stage. With respect to Gh3, no homology was found to known genes.

TABLE 1

Comparison between cotton fiber ACP and other plant ACPs

| | | Homology | |
|---|---|---|---|
| Plant | Source | DNA (%) | Amino acid (%) |
| Barley | leaf | 65 | 67 |
| Arabidopsis | chromosome | 65 | 61 |
| Spinach | leaf | 68 | 59 |
| Corn | seedling | 65 | 59 |
| *Cuphea lanceolata* | embryo | 69 | 61 |
| *Brassica napus* (rape) | embryo | 69 | 58 |

EXAMPLE 3

Cloning of Gene Associated with Cotton Fiber Formation

1. Preparation of poly(A)⁺RNA

The cotton plant, Supima (*Gossypium barbadense*), cultivated in a field was used as the test material. The ovules on the 5th day to the 15th day after flowering (fiber elongation stage) and those on the 25th day to the 30th day after the flowering (fiber non-elongation stage) were collected, and cotton fibers were separated from the seeds. About 5 g of each of the cotton fibers thus obtained was immediately frozen in liquid nitrogen and pulverized with a mortar in the presence of liquid nitrogen. To the pulverized cotton fibers was added 10 ml of 0.2 M Tris-acetate buffer for extraction [containing 5 M guanidinethiocyanate, 0.7% β-mercaptoethanol, 1% polyvinylpyrrolidone (M.W., 360,000) and 0.62% sodium N-lauroylsarcosinate, pH 8.5], and the mixture was further pulverized with a polytron homogenizer (manufactured by KINEMATICA Co.) under ice cooling for 2 minutes. At that time, β-mercaptoethanol and polyvinylpyrrolidone were incorporated into the buffer just before use. The pulverized mixture was centrifuged at 17,000×g for 20 minutes, and the supernatant was collected.

The supernatant was filtered through a miracroth, and the filtrate was gently overlaid on 1.5 ml of 5.7 M aqueous cesium chloride solution in a centrifuge tube, followed by centrifugation at 155,000×g for 20 hours at 20° C. The supernatant was discarded, and the precipitated RNA was collected. The precipitate was dissolved in 3 ml of 10 mM Tris-HCl and 1 mM EDTA-2Na, pH 8.0 (referred to as TE buffer), to which a mixture of phenol, chloroform and isoamyl alcohol (volume ratio, 25:24:1) was added at the same volume. The mixture was well agitated and then centrifuged at 17,000×g for 20 minutes, and the upper aqueous layer was collected. To the aqueous layer obtained were added a 0.1-fold volume of 3 M aqueous sodium acetate solution (adjusted to pH 6.2 by addition of gracious acetic acid) and a 2.5-fold volume of ethanol. The mixture was well agitated and allowed to stand without disturbance at −20° C. overnight. The mixture was then centrifuged at 17,000×g for 20 minutes, and the precipitate was washed with 70% ethanol and dried in vacuo.

The dry product was dissolved in 500 $\mu$l of TE buffer to give a solution of the whole RNA. This RNA solution was incubated at 65° C. for 5 minutes and then immediately cooled on ice, to which 2×coupling buffer (10 mM Tris-HCl, 5 mM EDTA-2Na, 1M NaCl, 0.5% SDS, pH 7.5) was added at the same volume. The mixture was overlaid on an oligo-dT cellulose column (manufactured by Clontech, Co.) which had been previously equilibrated with equilibration buffer (10 mM Tris-HCl, 5 mM EDTA-2Na, 0.5 M NaCl, 0.5% SDS, pH 7.5). The column was then washed with an about 10-fold volume of the equilibration buffer, and the poly(A)$^+$RNA was eluted with elution buffer (10 mM Tris-HCl, 5 mM EDTA-2Na, pH 7.5).

To the eluate obtained were added a 0.1-fold volume of the 3M aqueous sodium acetate solution and a 2.5-fold volume of ethanol, and the mixture was allowed to stand without disturbance at −70° C. The mixture was then centrifuged at 10,000×g, and the precipitate was washed with 70% ethanol and dried in vacuo. The dry product was dissolved again in 500 $\mu$l of TE buffer, and purification was repeated with an oligo-dT cellulose column. The poly(A)$^+$ RNA obtained from the cotton fibers at the fiber elongation stage was used for preparation of a cDNA library and a cDNA probe for differential screening, and the poly(A)$^+$ RNA obtained from the cotton fibers at the fiber non-elongation stage was used for preparation of a cDNA probe for differential screening.

2. Preparation of cDNA Library Specific to Fiber Elongation Stage

A cDNA library was prepared with ZAP-cDNA Synthesis Kit (manufactured by Stratagene Co.). The poly(A)$^+$RNA obtained from the cotton fibers at the fiber elongation stage in section 1 as a template, and double-stranded cDNA was synthesized by reverse transcriptase with oligo(dT) primer according to the method of Gubler and Hoffman et al. [Gene, 25, 263–269 (1983)].

To both ends of the cDNA obtained were ligated EcoRI adaptors (each having XhoI and SpeI sites in the inside), and the ligated DNA was digested with XhoI. The fragment was then ligated between the EcoRI and XhoI sites of the λ phage vector, λ ZAPII arm, and the vector was packaged with an in vitro packaging kit (manufactured by Stratagene Co., GIGAPACK Gold), followed by infection into E. coli strain SURE ($OD_{660}$=0.5), which afforded a number of recombinant λ phages serving as the cDNA library specific to the fiber elongation stage. This cDNA library had a size of 5.0×10$^6$.

3. Preparation of Probes

The poly(A)$^+$RNA prepared from the cotton fibers at the fiber elongation stage or at the fiber non-elongation stage was used as a template, cDNA was synthesized by reverse transcriptase M-MLV (manufactured by Toyobo Co., Ltd.) with oligo(dT) primer. After the synthesis, alkali treatment was carried out to remove the poly(A)$^+$RNA by hydrolysis. The cDNA thus obtained was used as a template, and a $^{32}$P-labelled probe was prepared with Random Primed DNA Labeling Kit (manufactured by USB Co.).

The $^{32}$P-labelled probes thus prepared by the cDNA obtained from the cotton fibers at the fiber elongation stage and by the cDNA obtained from the cotton fibers at the fiber non-elongation stage were used as a positive probe and as a negative probe, respectively, for differential screening.

4. Screening of Gene Associated with Fiber Formation and Elongation

The above λ phages constituting the cDNA library from the cotton fibers at the fiber elongation stage were infected into E. coli cells, which were grown on LB agar medium. About 50,000 plaques of λ phage DNA were replicated on two nylon membranes (Hybond-N, manufactured by Amersham Corp.).

The nylon membranes having replicated λ phage DNA thereon were transferred on a filter paper containing a solution for alkali denaturation (0.5 M NaOH, 1.5 M NaCl) and then allowed to stand for 4 minutes. The nylon membranes were transferred on a filter paper containing a solution for neutralization (0.5 M Tris-HCl, 1.5 M NaCl, pH 8.0) and then allowed to stand for 5 minutes. After washing with 2×SSC (0.3 M NaCl, 0.03 M trisodium citrate), these membranes were subjected to DNA fixation with Stratalinker (manufactured by Stratagene Co.). The membranes thus treated for DNA fixation were prehybridized in hybridization buffer [50% formamide, 0.5% SDS, 6×SSPE (3M NaCl, 0.2 M $NaH_2PO_4$, 20 mM EDTA-2Na, pH 7.4), 5×Denhardt solution (0.1% Ficoll, 0.1% polyvinylpyrrolidone, 0.1% bovine serum albumin), 50 $\mu$g/ml denatured salmon sperm DNA] at 42° C. for 3 hours, and the cDNA probes prepared in section 3 were separately added to the respective membranes, followed by hybridization at 42° C. for 20 hours. Thereafter, the membranes were removed and washed with solutions each containing 2×SSC, 1×SSC, 0.5×SSC or 0.1% SSC at 42° C. for 1 to 2 hours. These membranes were dried and then exposed overnight to X-ray films by allowing to closely adhere thereto.

As a result, 34 positive clones capable of hybridizing more strongly with the positive probe (for the fiber elongation stage) than with the negative probe (for the fiber non-elongation stage) were selected. The analysis was carried out for one of these positive colones, which was designated KC22.

KC22 has a partial homology with the gene of soybean exhibiting brassino-steroid-regulated protein (BRU1) [D. M. Zurek and S. D. Clouse, Plant Physiol (ROCKV) 102, 132 (1993)]; the gene coding for xyloglucan transferase of Vigna angularis, Glycine max or the like [Nishitani et al., J. Bio. Chem., 268, 25364–25368 (1993)]; and the meri-5 gene exhibiting specific expression to the apical meristem of Arabidopsis [J. I. Medford, J. S. Elmer, and H. J Klee, Plant Cell, 3, 359–370 (1991)].

Figure 9:
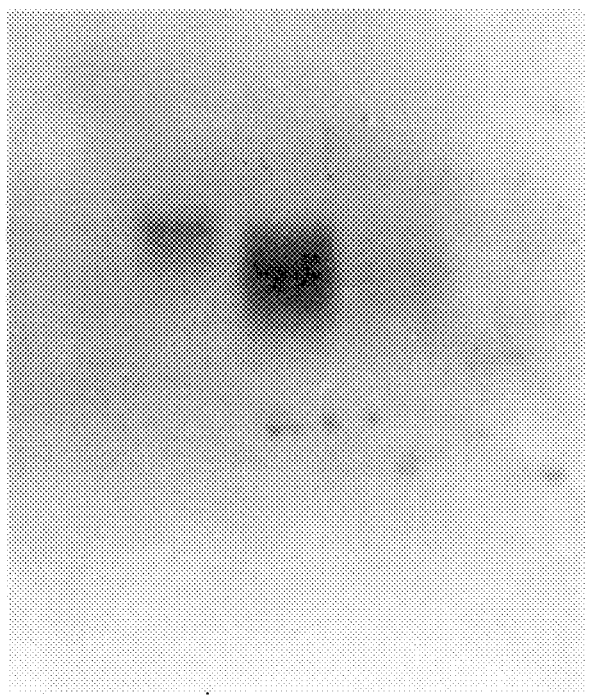
FIG. 9 is a photograph showing the results of Northern analysis of KC22. The specific gene expression of KC22 with brassinolide was revealed; lane 1, in vivo fiber RNA from Coker 312 (*Gossypium hirstum*) (from an intact ovule on the 7th day after the flowering, control); lane 2, in vitro fiber RNA with $10^{-6}$ M brassinolide (from an ovule culture prepared for 7 days, present invention); and lane 3, in vitro fiber RNA control (from an ovule culture prepared for 7 days, control).

Further, Northern analysis was carried out on the brassinolide-treated group and on the control group as follows. Cotton fibers were obtained from an ovule culture (in vitro) which had been prepared on a medium containing 1 $\mu$M brassinolide for 7 days and from an ovule culture (in vitro) which had been prepared on a medium containing no brassinolide in the same manner and from an intact ovule (in vivo) on the 7th day after the flowering. RNA was isolated from these three kinds of cotton fibers and examined for the degree of KC22 gene expression. The results of Northern analysis are shown in FIG. 9. As can be seen from comparison between lane 2 and lane 3, KC22 was highly expressed in the cotton fibers obtained from the ovule culture which had been prepared on a medium containing 1 μM brassinolide. This clearly indicates that the expression of KC22 gene is regulated by brassinolide.

From the phage DNA of KC22, plasmid clone pKC22 having a cDNA insert was prepared by the in vivo excision method with ZAP-cDNA Synthesis Kit (manufactured by Stratagene Co.).

First, 200 μl of a KC22-containing phage solution was mixed with 200 μl of *E. coli* XL1-Blue suspension and 1 μl of helper phage R408 suspension, and the mixture was incubated at 37° C. for 15 minutes, to which 3 ml of 2×YT medium was added. Shaken cultures were grown at 37° C. for 2 hours and then treated at 70° C. for 20 minutes, followed by centrifugation at 4000×g for 10 minutes, and the supernatant was collected. Then, 30 μl of the supernatant was mixed with 30 μl of *E. coli* SOLR suspension, and the mixture was incubated at 37° C. for 15 minutes and then inoculated on several microliters of LB agar medium containing 50 ppm ampicillin, followed by incubation at 37° C. overnight. The colony-forming *E. coli* contained the plasmid clone pKC22 having the cDNA insert.

The nucleotide sequence of the cDNA insert in the plasmid pKC22 was determined by the dideoxy chain termination method [Messing, Methods in Enzymol., 101, 20–78 (1983)]. The nucleotide sequence and deduced amino acid sequence are shown in the Sequence Listing, SEQ ID NOs: 3 (clone KC22) and 4, respectively. These sequences correspond to the cDNA nucleotide sequence and amino acid sequence, respectively, of a gene capable of changing the degree of its expression at the fiber formation and elongation stage.

5. Expression of Desired Gene in *E. coli*

The transformants obtained above (in the case of KC22) were suspended in 50 ml of LB medium containing 100 μg/ml of ampicillin, and shaken cultures were grown at 37° C. When the turbidity $OD_{660}$ of the shaken cultures became 0.2, isopropyl-β-thiogalactopyrenosido (IPTG) was added to yield a final concentration of 10 mM. The shake cultures were further grown at 37° C. until the turbidity $OD_{660}$ became 1.0. After completion of the culturing, bacterial cells were collected by centrifugation at 1600×g for 15 minutes. The collected bacterial cells were suspended in a 4-fold volume of lysis buffer [50 mM Tris-HCl (pH 8.0), 1 mM EDTA-2Na, 1 μM PMSF (phenylmethylsulfonyl fluoride), 10% sucrose], to which Lysozyme (manufactured by Sigma Co.) was added to yield a final concentration of 1 mg/ml, followed by allowing to stand on ice without disturbance for 10 minutes. After 10 minutes, non-ionic surfactant Nonidet P-40 (manufactured by Sigma Co.) was added to the cell suspension to yield a final concentration of 1%, and the mixture was further allowed to stand on ice without disturbance for 10 minutes, followed by centrifugation at 48,000×g for 1 hour. To the supernatant obtained was added 2×Laemli sample buffer [0.125 M Tris-HCl (pH 6.8), 20% glycerol, 10% β-mercaptoethanol, 6% SDS, 0.1% bromophenol blue] at the same volume, and the mixture was boiled for 2 minutes, followed by SDS-polyacrylamide gel electrophoresis (SDS-PAGE). After completion of the electrophoresis, the gel was stained with Coomassie brilliant blue (CBB) and decolorized with 7% acetic acid and 25% methanol. A band was observed near the position corresponding to the molecular weight of 39 kDa as desired, and the expression of the desired gene was thus confirmed.

6. Preparation of Transformed *Arabidopsis thaliana*

(1) Construction of Plasmid

Figure 10:
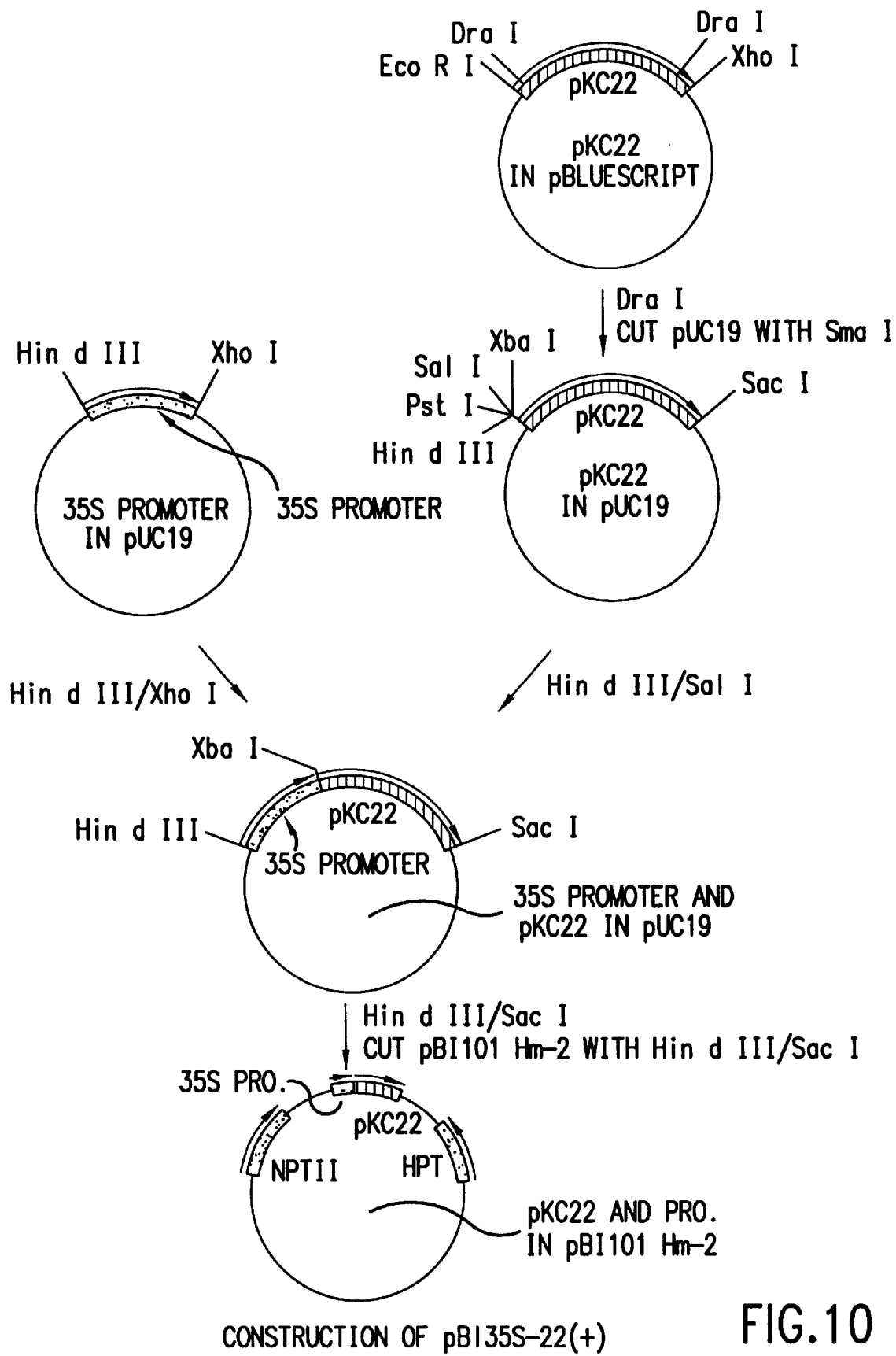
FIG. 10 is a diagram showing the construction of plasmid pBI35S-22(+).

The nucleotide sequence of KC22 as shown by SEQ ID NO: 3 was digested with DraI so as to contain the whole open reading frame thereof. The DraI fragment was subcloned in the SmaI site of pUC19. This plasmid was digested with SalI and HindIII, in which the HindIII-XhoI fragment of 35S promoter was subcloned. This clone was digested with HindIII and SacI, and the HindIII-SacI fragment was subcloned between the HindIII site and the SacI site of binary vector pBI101-Hm2. The plasmid thus obtained was designated pBI35S-22(+). The construction of this plasmid is shown in FIG. 10. The transformed *E. coli* JM109 was designated *E. coli* JM109/pBI35S-22(+).

In the same manner as described above, a plasmid containing the nucleotide sequence of KC22 in anti-sense direction was prepared. The plasmid thus obtained was designated pBI35S-22(−). The transformed *E. coli* JM109 was designated *E. coli* JM109/pBI35S-22(−).

(2) Introduction of Plasmid into Agrobacterium

The *E. coli* JM109/pBI35S-22(+) obtained in section 6(1) and the *E. coli* strain HB101 containing helper plasmid pRK2013 were separately cultured on LB medium containing 50 mg/l of kanamycin at 37° C. overnight, while the Agrobacterium strain EHA101 was cultured on LB medium containing 50 mg/l of kanamycin at 37° C. over two successive nights. Then, bacterial cells were harvested by taking 1.5 ml of each of the cultures in an Eppendorf tube, and then washed with LB medium. These bacterial cells were suspended in 1 ml of LB medium, after which three kinds of bacteria were mixed together in 100 μl portions. The mixture was plated on LB agar medium and incubated at 28° C. for ensuring the conjugation transfer of plasmids to Agrobacterium. After 1 to 2 days, a part of the medium was scratched by means of a sterile loop, and spread over LB agar medium containing 50 mg/l kanamycin, 20 mg/l hygromycin B and 25 mg/l chloramphenicol. The incubation was continued at 28° C. for 2 days, and a single colony was selected. The transformant thus obtained was designated EHA101/pBI35S-22(+).

In the same manner as described above, transformant EHA101/pBI35S-22(−) was prepared from *E. coli* JM109/pbI35S-22(−) obtained in section 6(1).

(3) Cultivation of Sterile *Arabidopsis thaliana*

Several dozens of seeds of *Arabidopsis thaliana* stain Wassilewskija (hereinafter referred to as strain WS; furnished by Dr. Shinmyo in Osaka University) were placed in a 1.5-ml tube, to which 1 ml of 70% ethanol was added, and the seeds were allowed to stand for 3 minutes. The seeds were immersed in a solution for sterilization (5% sodium hypochlorite, 0.02% Triton X-100) for 3 minutes, washed five times with sterile water, and then sowed in MSO plate (4.6 g of Murashige-Skoog inorganic salts, 10 g of sucrose, 1 ml/liter 1000×vitamin stock solution, pH 6.2). This plate was allowed to stand at 4° C. for 2 days for low-temperature treatment and then cultivated at 22° C. in a plant incubator (model MLR-350HT, manufactured by Sanyo Electric Co., Ltd.) under long-day conditions (16 hours light and 8 hours dark) at a light intensity of 6000 lux for 10 days.

(4) Infection with Agrobacterium

The roots of several pieces of the above strain WS cultivated for 10 days in section 6(3) were gathered together, cut with a surgical knife to have a uniform length of about 1.5 to 2.0 cm, and placed in order on CIM plate (prepared by adding 2,4-dichlorophenoxyacetic acid and kinetin to MSO plate to yield a final concentration of 0.5 μg/ml and 0.05 μg/ml, respectively). These root explants were cultivated under long-day conditions (16 hours light and 8 hours dark) at a light intensity of 3000 lux for 2 days. MS diluent (6.4 g/liter Murashige-Skoog inorganic salts, pH 6.3) was 3-fold diluted and dispensed in 1 ml portions into tubes, in which the roots in callus form were immersed for 10 minutes. These explants were placed in order on two layers of sterile filter papers to remove excess water, transferred on fresh CIM plate, and cocultivated for 2 days under the same conditions as described above.

(5) Sterilization

The explants grown to a degree enough to observe the respective bacterial strains with the naked eye were placed in a solution for sterilization (prepared by adding claforan to MS diluent to yield a final concentration of 200 μg/ml), followed by washing with gentle shaking for 60 minutes. After five repetitions of this procedure, these explants were placed on a sterile filter paper to remove water, placed in order on SIMC plate (prepared by adding $N^6$-[2-isopentenyl] adenine, IAA and claforan to MSO plate to yield of a final concentration of 5 μg/ml, 0.15 μg/ml and 500 μg/ml, respectively), and cultivated under long-day conditions (16 hours light and 8 hours dark) at a light intensity of 6000 lux for 2 days.

(6) Selection of Transformed Plants

The above explants cultivated for 2 days in section 6(5) were transplanted on SIMCS plate (prepared by adding hygromycin B to SIMC plate to yield a final concentration of 4.6 U/ml) and cultivated under long-day conditions (16 hours light and 8 hours dark) at a light intensity of 6000 lux. Thereafter, these explants were transplanted on fresh SIMCS plate every week. The transformed explants were continuously grown to become dome-shaped swollen calli, while the color of non-transformants changed to brown. The calli of the transformants exhibited green color after about 2 weeks. After about 1 month, shoots were formed.

(7) Regeneration of Transformed Plants

Shoots were cut with a razor or a surgical knife so as not to include any callus, and slightly inserted into RIM plate as if they were placed thereon. After 8 to 10 days, the plant having several roots of about 1 to 2 cm in length was transplanted with a pincette in a mini-pot of rock wool (manufactured by NITTO BOSEKI CO., LTD) soaked with inorganic salts medium [5 mM $KNO_3$, 2.5 mM K-phosphate buffer (pH 5.5), 2 mM $MgSO_4$, 2 M $Ca(NO_3)_2$, 50 μM Fe-EDTA, 1000×microelements (70 mM $H_3BO_3$, 14 mM $MnCl_2$, 0.5 mM $CuSO_4$, 1 mM $ZnSO_4$, 0.2 mM $Na_2MoO_4$, 10 mM NaCl, 0.01 mM $CoCl_2$) 1 ml/liter], and cultivated. After flowering and podding, these plants were transplanted in the soil which was prepared by mixing pearlite and vermiculite (manufactured by TES Co.) at a ratio of 1:1 and soaking in inorganic salts medium. After about 1 month, a few hundred of seeds per plant were obtained. These seeds are hereinafter referred to as T1 seeds.

(8) Selection of Antibiotic-resistant Strains

About one hundred T1 seeds were sterilized by the same method as described in section 6(3), and then sowed in MSH plate. Hygromycin B-resistant strains were germinated at a ratio of approximately 3:1.

7. DNA Extraction and Southern Hybridization

The T1 seeds germinated in section 6(8) were transplanted with a pincette in a mini-pot of rock wool soaked with inorganic salts medium, and cultivated at 22° C. under long-day conditions (16 hours light and 8 hours dark) at a light intensity of 6000 lux. After 2 weeks, the aerial parts of the plants were cut with a surgical knife as if the surface of the rock wool was smoothed with a knife, and immediately frozen with liquid nitrogen. The frozen aerial parts were finely pulverized with a mortar in the presence of liquid nitrogen, to which 3 ml of DNA extraction buffer [200 mM Tris-HCl (pH 8.0), 100 mM EDTA-2Na, 1% sodium N-lauroylsarcosinate, 100 μg/ml proteinase K] was added, and the mixture was well agitated and then incubated at 60° C. for 1 hour, followed by centrifugation at 10,000×g for 10 minutes. The supernatant was filtered through a miracloth, and the filtrate was transferred in a new tube. After three extractions with a mixture of phenol, chloroform and isoamyl alcohol (25:24:1), ethanol precipitation was carried out. The precipitate was dissolved in TE buffer. From about 2.0 g of the plants, 20 μg of genomic DNA was obtained. Each 1 μg of genomic DNA was digested with EcoRI and HindIII, and the DNA fragments were subjected to 1% agarose electrophoresis and Southern hybridization.

In the same manner as described, the non-transformed seeds of the WS strain were germinated and grown, after which DNA isolated from the plants was digested with EcoRI and HindIII, and the DNA fragments were subjected to 1% agarose gel electrophoresis and Southern hybridization. As the probe for hybridization, pKC22 was used.

Southern hybridization was carried out according to the method described in Molecular Cloning, A Laboratory Manual, ch. 9, pp. 31–58 (Cold Spring Harbor, 1989). That is, each DNA sample was subjected to 1% agarose gel electrophoresis, followed by alkali denaturation and overnight Southern blotting on a nylon membrane (Hybond-N, manufactured by Amersham Corp.). The membrane was irradiated with an UV trans-illuminator (254 nm) for 3 minutes to cause DNA fixation. This membrane was prehybridized in 5 ml of prehybridization buffer [5×Denhardt solution, 6×SSC, 0.1% SDS, 10 μg/ml salmon sperm DNA] at 50° C. for 2 hours, followed by hybridization with a probe at 50° C. overnight. The membrane was washed twice with a washing solution containing 2×SSC and 0.1% SDS at room temperature for 10 minutes and then twice with the same solution at 50° C. for 30 minutes. After the membrane was dried, autoradiograms were prepared by exposing the membrane to an X-ray film (manufactured by Eastman Kodak Co.) in a cassette to at −80° C. overnight. Comparison of signal patterns detected by Southern hybridization was made among: (i) the non-transformants; (ii) the transformants having pKC22; and (iii) the transformants having only the vector.

Specific signals from the transformants (ii) were observed at positions of about 1.6 and 0.7 kbp for the EcoRI-digested sample and at a position of about 6 kbp for the HindIII-digested sample, in addition to endogenous signals common to (i), (ii) and (iii), indicating that the desired gene was incorporated in the transformants (ii).

EXAMPLE 4

Comparison of Height Between Transformed Plant and Wild-type Plant

Figure 11:
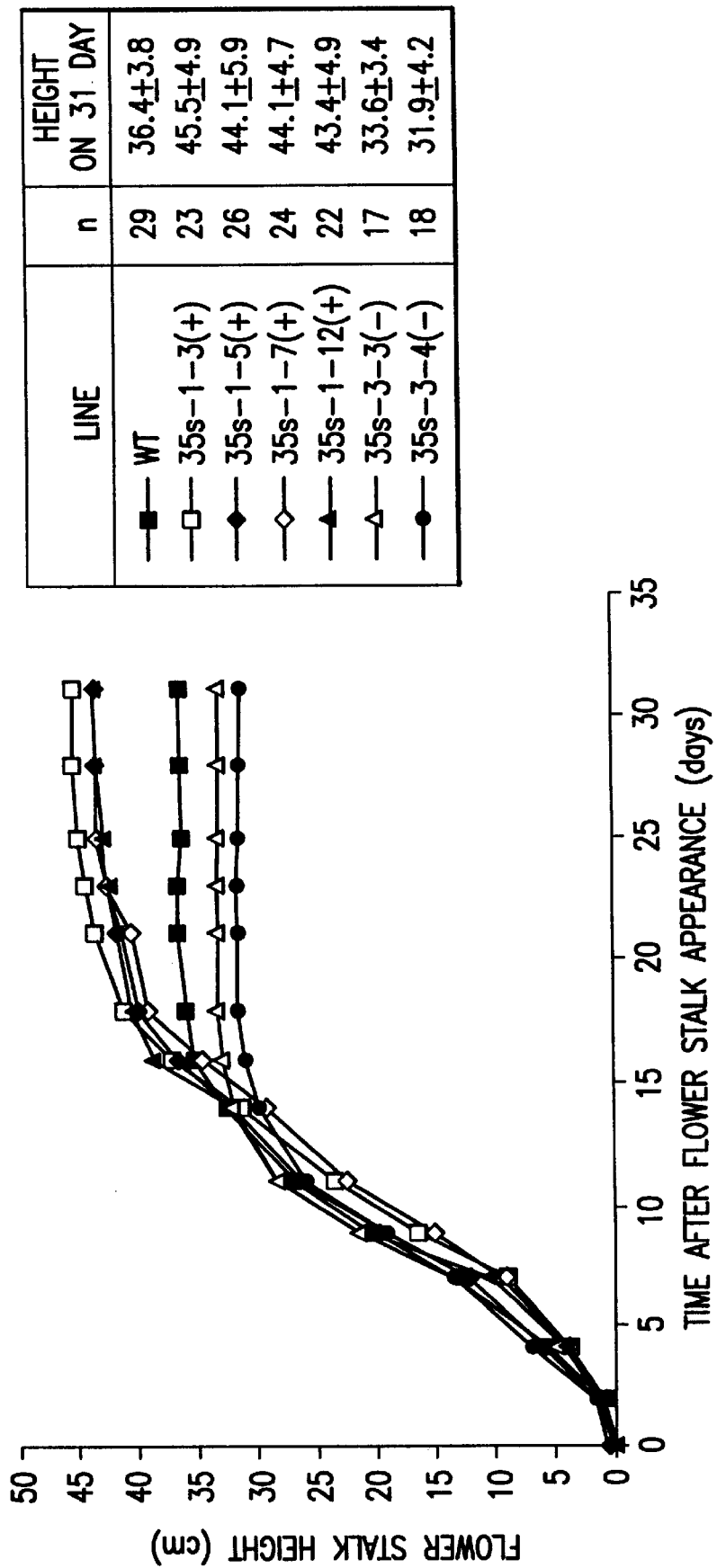
FIG. 11 is a graph showing the change of flower stalk height (length) in transgenic *Arabidopsis thaliana* expressing the KC22 gene construct and untransferred Arabidopsis plants with a lapse of time. In the note of this graph, "n" means the number of replications (the number of samples).
Figure 12:
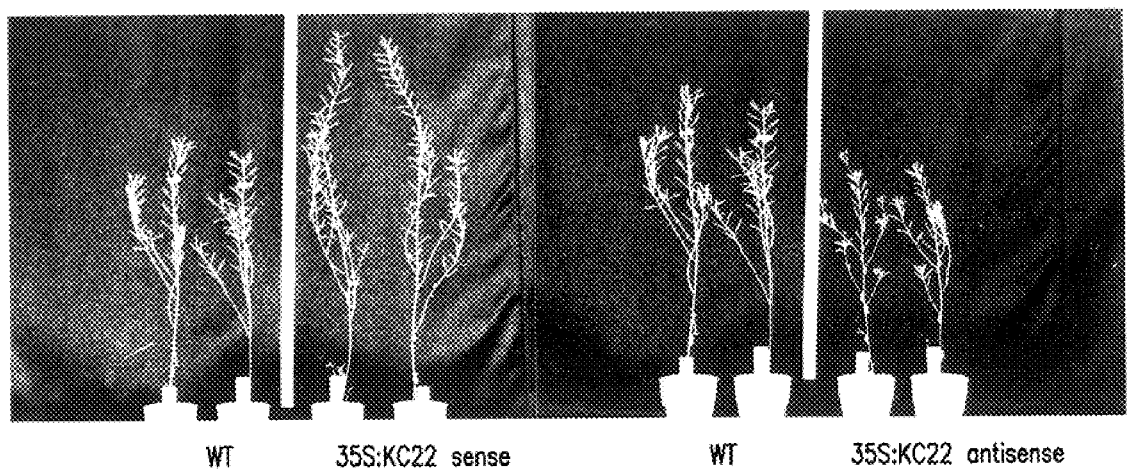
FIG. 12 are photographs showing the comparison of height between the wild-type plant and the transformed plant containing sense 35S-KC22 and between the wild-type plant and the transformed plant containing anti-sense 35S-KC22, respectively.

For wild-type *Arabidopsis thaliana* and transformed *Arabidopsis thaliana* prepared in Example 3, section 6, 100 seeds were placed on a water-containing filter paper and allowed to absorb water at 4° C. for 2 days. These seeds were then sown in 25 pots at a ratio of about 4 seeds per pot. For cultivation were used rock wool minipots containing a 1:1 mixture of perlite and vermiculite. These pots were provided with water containing Hyponex® (Murakami Bussan Kabushiki Kaisha), and the plants were cultivated under continuous light in a cultivation room at 22° C. After the sowing, these two kinds of plants were germinated approximately at the same time. On the 10th day after the sowing, the best grown plant was left and the other three plants were thinned out. The plant was then examined for the change of height (flower stalk length) with a lapse of time. The relationship between the time after the flower stalk appearance and the height is graphically shown in FIG. 11. The height on the 51st day after the sowing, at which the growth was stopped, was compared, and it was found that the transformed plant containing sense gene 35S-KC22(+) had an increased height as compared with the wild-type plant, whereas the transformed plant containing anti-sense gene 35S-KC22(−) had the same or a decreased height as compared with the wild-type plant. The photographs of the wild-type *Arabidopsis thaliana* and transformed *Arabidopsis thaliana* are shown in FIG. 12.

What is claimed is:

1. An isolated gene that is expressed during the formation or elongation of cotton fibers and that hybridizes to SEQ ID NO: 1, 3, 5, 7 or 9 in the presence of: 50% formamide; 0.5% SDS; 6×SSPE; 5×Denhardt solution; and 50 µg denatured salmon sperm DNA at 42° C., followed by washing with a solution containing 0.1×SSC at 42° C., wherein said gene is isolated from ovules or fibers of a cotton plant.

2. An isolated gene that is expressed during the formation or elongation of cotton fibers and that hybridizes to SEQ ID NO: 1, 3, 5, 7 or 9 in the presence of: 50% formamide; 0.5% SDS; 6×SSPE; 5×Denhardt solution; and 50 µg denatured salmon sperm DNA at 42° C., followed by washing with a solution containing 0.1×SSC at 42° C., wherein said gene is isolated from a cotton plant.

3. An isolated DNA molecule comprising an anti-sense sequence to the gene of claim 1 or 2.

4. A recombinant vector comprising the gene of claim 1 or 2 or comprising an anti-sense sequence to said gene.

5. A transgenic plant obtained by transforming a plant cell with a recombinant vector comprising the gene of claim 1 or 2, or comprising an anti-sense sequence to said gene, resulting in a transformed plant cell, and regenerating a transgenic plant from the transformed plant cell.

6. A method for producing cotton fibers, which comprises transforming a cotton cell with a recombinant vector comprising the gene of claim 1 or 2, or comprising an anti-sense sequence to said gene, resulting in a transformed cotton cell, regenerating a transgenic cotton plant from the transformed cotton cell, cultivating the transgenic cotton plant to produce cotton bolls, and collecting cotton fibers from the cotton bolls.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 1378 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:1:

```
GAATCCCCCT CCTCTTTTGT TGTGAAGAAA AAAATGGTTG GGCTGTTTAG GTTGGTGAGT      60
GGGTGTCCGG GACCAAGTGG CTTTGGTTCA GCCTCCACCG CCCAAGAGGT TACCGAAGGG     120
ATTGATGGAA CCAACTTGAC TGCTCTAGTT ACCGGAGGAG CAAGTGGAAT TGGGTTGGAA     180
ACTTCTAGAG TATTGGCTCT TCGTGGAGTC CACGTCATCA TCGGTGCAAG GAACATGAAA     240
GCCGCGAATG AAGCAAAGAA CAAAATTGTT AGAGAGAACC CAAGAGCCCG TATAGATGTT     300
CTGGAGCTGG ATCTTTGCTC TACTAATTCA ATCAGATCAT TTGCCGACAA TTTCATTGCT     360
CTTCATCTTC CTCTCAATAT CTTAATAAAC AATGCTGGCA TCATGTTTTG TCCCTTTCAG     420
CTTTCTCAAA ATGGATTAGA GGTGCAGTTT GCAACTAATC ATATAGGACA TTTCCTCTTA     480
ACAAACCTTC TACTGGACAC AATGAAGAAC ACAGTTAAAG CAACTGGGAT CCAAGGAAGG     540
GTTGTCAACT TATCATCAAT AGCTCACAAC TACTGTTATA AGAAAGGGAT CCGATTTCAT     600
AAGATCAATG ACAAGCAAGG ATACAGTGAG AAAAGAGCAT ATGGGCAGTC CAAATTAGCA     660
AATATATTGC ATGCCAATGA ACTCTCTCGT CGGTTGCAGG AGGAGGGTGT GAACATCACA     720
GTTAATTCGG TTCACCCGGG ATTGATTATG ACGCCTCTGT TTAGACACTC CGCTGATCTG     780
ATGAAACTTT TGAAGTTCTT CAGTTTCTTT CTCTGGAAGA ACGTTCCTCA GGGGGCAGCT     840
ACGACGTGCT ACGTCGCGCT CCACCCGCGA CTCAATGGGG TGACCGGAAA ATACTTTGCG     900
GACTGCAATG AGATGAGACC AAGTTCATAT GCTAGAAATG AGTCCTTGGG AAGGGAGCTT     960
TGGGAATTCA GTAACAAATT GATTAGCTCA GTTTCAGAAC CTTAACTCAG ATCATCACCT    1020
CTCTTTCCAA ATGGCAAAAA AAAAAAAAAA TTGCACTTAC GTATTTTCAC ATTAAATGGG    1080
GTTTCCTCCA TGGCATGGCA TGAATGAAGG GATGATTTTC AGCATGGGAA ATCTTGAAGC    1140
ATAATAATAA GCTTAAAGTG CCTTTTACTT TCTCGTTTTC GTGTTAAAGG CATCATACTA    1200
TCATAGCAGT TGGTTTCCTA ATATGTGTGA ATTTTCAGTG TTTCAAAGGA ATAAAATTCT    1260
TTCTATATTA TTCATATTAG TTTATTTTAT ACGGATTAAT TATTGTATGT ATCATTTTAA    1320
TTATATTATA ATCATATTAT TCAATATACA TATTCTTACT AAAAAAAAAA AAAAAAAA     1378
```

-continued (2) INFORMATION FOR SEQ ID NO:2:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Gly Leu Phe Arg Leu Val Ser Gly Cys Pro Gly Pro Ser Gly
 1               5                  10                  15

Phe Gly Ser Ala Ser Thr Ala Gln Glu Val Thr Glu Gly Ile Asp Gly
                20                  25                  30

Thr Asn Leu Thr Ala Leu Val Thr Gly Gly Ala Ser Gly Ile Gly Leu
            35                  40                  45

Glu Thr Ser Arg Val Leu Ala Leu Arg Gly Val His Val Ile Ile Gly
50                  55                  60

Ala Arg Asn Met Lys Ala Ala Asn Glu Ala Lys Asn Lys Ile Val Arg
65                  70                  75                  80

Glu Asn Pro Arg Ala Arg Ile Asp Val Leu Glu Leu Asp Leu Cys Ser
                85                  90                  95

Thr Asn Ser Ile Arg Ser Phe Ala Asp Asn Phe Ile Ala Leu His Leu
            100                 105                 110

Pro Leu Asn Ile Leu Ile Asn Asn Ala Gly Ile Met Phe Cys Pro Phe
        115                 120                 125

Gln Leu Ser Gln Asn Gly Leu Glu Val Gln Phe Ala Thr Asn His Ile
    130                 135                 140

Gly His Phe Leu Leu Thr Asn Leu Leu Leu Asp Thr Met Lys Asn Thr
145                 150                 155                 160

Val Lys Ala Thr Gly Ile Gln Gly Arg Val Val Asn Leu Ser Ser Ile
                165                 170                 175

Ala His Asn Tyr Cys Tyr Lys Lys Gly Ile Arg Phe His Lys Ile Asn
            180                 185                 190

Asp Lys Gln Gly Tyr Ser Glu Lys Arg Ala Tyr Gly Gln Ser Lys Leu
        195                 200                 205

Ala Asn Ile Leu His Ala Asn Glu Leu Ser Arg Arg Leu Gln Glu Glu
    210                 215                 220

Gly Val Asn Ile Thr Val Asn Ser Val His Pro Gly Leu Ile Met Thr
225                 230                 235                 240

Pro Leu Phe Arg His Ser Ala Asp Leu Met Lys Leu Leu Lys Phe Phe
                245                 250                 255

Ser Phe Phe Leu Trp Lys Asn Val Pro Gln Gly Ala Ala Thr Thr Cys
            260                 265                 270

Tyr Val Ala Leu His Pro Arg Leu Asn Gly Val Thr Gly Lys Tyr Phe
        275                 280                 285

Ala Asp Cys Asn Glu Met Arg Pro Ser Ser Tyr Ala Arg Asn Glu Ser
    290                 295                 300

Leu Gly Arg Glu Leu Trp Glu Phe Ser Asn Lys Leu Ile Ser Ser Val
305                 310                 315                 320

Ser Glu Pro
```

(2) INFORMATION FOR SEQ ID NO:3:

(i) SEQUENCE CHARACTERISTICS:
        (A) LENGTH: 1035 base pairs
        (B) TYPE: nucleic acid -continued (C) STRANDEDNESS: double
        (D) TOPOLOGY: linear (ii) MOLECULE TYPE: cDNA to mRNA (xi) SEQUENCE DESCRIPTION: SEQ ID NO:3:

| | |
|---|---|
| CAATAATTCT CTCTGTTTCT CTGGTTTAAA CATGGGTATG GGTTTAAGGA ATGGATTTCT | 60 |
| TTTGATTTTA TCTTGTGTTG TTACACTTTC CCTCTCAGTT TTGGGGCGAC CTGCCACTTT | 120 |
| CCTTGAAGAT TTTAGAATCA CTTGGTCTGA TTCTCATATT AGGCAAATCG ATGGAGGGAG | 180 |
| AGCCATCCAA CTTGTTCTCG ACCAAAATTC AGGCTGTGGA TTTGCTTCTA AAAGGCAGTA | 240 |
| TTTGTTCGGA CGTGTCAGCA TGAAAATCAA GCTCATCCCC GGCGACTCCG CCGGAACAGT | 300 |
| CACCGCCTTT TATATGAATT CTGTTACAGA TGCTGTGCGA GATGAGCTAG ACTTCGAGTT | 360 |
| CTTGGGAAAC CGTACCGGGC AGCCATATAC GGTTCAAACC AATATCTATG CCCATGGAAA | 420 |
| GGGTGACAGG GAACAAAGGG TTAACCTTTG GTTCGATCCT GCTGCAGATT TCCATACTTA | 480 |
| CTCAATCATG TGGAACCATC ATCAGATTGT GTTCTATATT GATGAAGTGC AATTAGGGT | 540 |
| TTATAAGAAC AATGAAGCTA GAAATATCCC ATACCCAAAA CTCCAGCCAA TGGGAGTTTA | 600 |
| TTCAACGCTG TGGGAGGCTG ATGATTGGGC AACAAGGGGA GGTTTAGAGA AAATTGATTG | 660 |
| GACCAAAGCT CCGTTCTTAG CTTATTACAA GGACTTCGAC ATTGAAGGAT GTCCGGTTCC | 720 |
| AGGGCCAGTA AACTGTGCCA CAAACAGTAG GAACTGGTGG GAGGGCACTG CTTATCAAGC | 780 |
| CCTTAATGCC ATGGAAGCTA AAAGATATAG TTGGGTTCGT ATGAACCACG TGATATACGA | 840 |
| TTACTGCACC GACAAGTCCC GTTACCCGGT TACCCCACCG GAGTGCATGT CCATCATCTG | 900 |
| AAAATCCAAA CCCAAGTGAA GTTTCGTGTC CTATTTTACG TACATATGTA CCTCCCTTTA | 960 |
| TACAAATAAT AGAGCCATGC AAAAATTGGG TTTTAAAAAA AAAAAAAAA AAAAAAAAA | 1020 |
| AAAAAAAAAA AAAAA | 1035 |

(2) INFORMATION FOR SEQ ID NO:4:

(i) SEQUENCE CHARACTERISTICS:
        (A) LENGTH: 289 amino acids
        (B) TYPE: amino acid
        (D) TOPOLOGY: linear (ii) MOLECULE TYPE: protein (xi) SEQUENCE DESCRIPTION: SEQ ID NO:4:

Met Gly Met Gly Leu Arg Asn Gly Phe Leu Leu Ile Leu Ser Cys Val
1               5                   10                  15

Val Thr Leu Ser Leu Ser Val Leu Gly Arg Pro Ala Thr Phe Leu Glu
            20                  25                  30

Asp Phe Arg Ile Thr Trp Ser Asp Ser His Ile Arg Gln Ile Asp Gly
        35                  40                  45

Gly Arg Ala Ile Gln Leu Val Leu Asp Gln Asn Ser Gly Cys Gly Phe
    50                  55                  60

Ala Ser Lys Arg Gln Tyr Leu Phe Gly Arg Val Ser Met Lys Ile Lys
65                  70                  75                  80

Leu Ile Pro Gly Asp Ser Ala Gly Thr Val Thr Ala Phe Tyr Met Asn
                85                  90                  95

Ser Val Thr Asp Ala Val Arg Asp Glu Leu Asp Phe Glu Phe Leu Gly
            100                 105                 110

Asn Arg Thr Gly Gln Pro Tyr Thr Val Gln Thr Asn Ile Tyr Ala His
        115                 120                 125

```
Gly Lys Gly Asp Arg Glu Gln Arg Val Asn Leu Trp Phe Asp Pro Ala
    130                 135                 140

Ala Asp Phe His Thr Tyr Ser Ile Met Trp Asn His Gln Ile Val
145                 150                 155                 160

Phe Tyr Ile Asp Glu Val Pro Ile Arg Val Tyr Lys Asn Asn Glu Ala
                165                 170                 175

Arg Asn Ile Pro Tyr Pro Lys Leu Gln Pro Met Gly Val Tyr Ser Thr
            180                 185                 190

Leu Trp Glu Ala Asp Asp Trp Ala Thr Arg Gly Gly Leu Glu Lys Ile
        195                 200                 205

Asp Trp Thr Lys Ala Pro Phe Leu Ala Tyr Tyr Lys Asp Phe Asp Ile
    210                 215                 220

Glu Gly Cys Pro Val Pro Gly Pro Val Asn Cys Ala Thr Asn Ser Arg
225                 230                 235                 240

Asn Trp Trp Glu Gly Thr Ala Tyr Gln Ala Leu Asn Ala Met Glu Ala
                245                 250                 255

Lys Arg Tyr Ser Trp Val Arg Met Asn His Val Ile Tyr Asp Tyr Cys
            260                 265                 270

Thr Asp Lys Ser Arg Tyr Pro Val Thr Pro Pro Glu Cys Met Ser Ile
        275                 280                 285

Ile
```

(2) INFORMATION FOR SEQ ID NO:5:

(i) SEQUENCE CHARACTERISTICS:
        (A) LENGTH: 1041 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:5:

```
ATGGCTTTCA AAGCTCTGCT GCTGTTACTA TTGGCCACTT TTCTGCTTGT TTCAACAACA      60
GTTGCTTCCA ATGAAGTGGG AGTGAAGACT GAGATTAAAT ATGCTGCTCC TGTTCCAGTG     120
AAGGCACCTA TCCCTGCTCC ACCCGTTAAG CCTCCCACCA CTCCGGTGCC GCCGTACAAG     180
GCTCCAACTC CAGCACCCCC AACTAAGGGC CCCACTCCAT ATAAACCCCC TACCAAGGCC     240
CCCACTCCAC CATATAAACC ACCAACCAAG GCTCCTACTC CACCATATAA ACCCCCAGCT     300
CCTGCACCAC CAACCAAGGC TCCTACTCCA CCATATAAGC CCCAGCTCC TGCACCACCA      360
ACCAAGGCTC CTACTCCACC ATATAAGCCC CCAGCTCCTG CACCACCAAC CAAGGCTCCA     420
ACTCCACCAT TTAAGCCCCC AGCACCAGCA CCACCAACCA AGGCTCCTAC TCCCCCATAT     480
AAACCCCCTA CTCCCGCACC GGCACCTCCA GTCAAGGCCC CTACTCCCCC ATATATGCCC     540
CCAACACCCC CAACCAAAGC ACCAACTCCA GCACCAGCAC CGCCAACTAA AGCACCAACT     600
CCCCCATATA AGCCCCCAGT TCCTACACCT CCAGTTAAGC CACCAACAAC TCCAGCACCG     660
CCTTACAAGC CACCAAGTCC ACCATTGCCA CCTGTTAGGA CAAAAAAGGA TTGCATCCCA     720
TTATGTGGAC AAAGGTGCAA ATTACACTCA AGGACTAACC TATGCTTGAG AGCTTGCATG     780
ACATGCTGTG ACAGATGCAA ATGTGTCCCA CCAGGGACAT ATGGCAACAG GGAAATGTGT     840
GGCAAATGTT ATACTGATAT GAGAACCCAC CGCAACAAGC ACAAATGTCC TTGAAAAGCC     900
CAACCAAAGC CCCCAAAAAA CGACACTTCT TGAGTATGTG TTTTTCATAT TTGTAATAGC     960
AAAAAAGCTT GCAGTAATAA GTTCTGTAAG AAGAGAGGAA ATGGATGGAT TTCTTGTAGT    1020
```

GTCAAAAAAA AAAAAAAAAA A                                                           1041

(2) INFORMATION FOR SEQ ID NO:6:

(i) SEQUENCE CHARACTERISTICS:
        (A) LENGTH: 297 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Phe Lys Ala Leu Leu Leu Leu Ala Thr Phe Leu Leu
1               5                   10                  15

Val Ser Thr Thr Val Ala Ser Asn Glu Val Gly Val Lys Thr Glu Ile
            20                  25                  30

Lys Tyr Ala Ala Pro Val Pro Val Lys Ala Pro Ile Pro Ala Pro Pro
            35                  40                  45

Val Lys Pro Pro Thr Thr Pro Val Pro Pro Tyr Lys Ala Pro Thr Pro
50                  55                  60

Ala Pro Pro Thr Lys Gly Pro Thr Pro Tyr Lys Pro Pro Thr Lys Ala
65                  70                  75                  80

Pro Thr Pro Pro Tyr Lys Pro Pro Thr Lys Ala Pro Thr Pro Pro Tyr
                85                  90                  95

Lys Pro Pro Ala Pro Ala Pro Pro Thr Lys Ala Pro Thr Pro Pro Tyr
                100                 105                 110

Lys Pro Pro Ala Pro Ala Pro Pro Thr Lys Ala Pro Thr Pro Pro Tyr
                115                 120                 125

Lys Pro Pro Ala Pro Ala Pro Pro Thr Lys Ala Pro Thr Pro Pro Phe
130                 135                 140

Lys Pro Pro Ala Pro Ala Pro Pro Thr Lys Ala Pro Thr Pro Pro Tyr
145                 150                 155                 160

Lys Pro Pro Thr Pro Ala Pro Ala Pro Pro Val Lys Ala Pro Thr Pro
                165                 170                 175

Pro Tyr Met Pro Pro Thr Pro Pro Thr Lys Ala Pro Thr Pro Ala Pro
                180                 185                 190

Ala Pro Pro Thr Lys Ala Pro Thr Pro Pro Tyr Lys Pro Pro Val Pro
                195                 200                 205

Thr Pro Pro Val Lys Pro Pro Thr Thr Pro Ala Pro Pro Tyr Lys Pro
210                 215                 220

Pro Ser Pro Pro Leu Pro Pro Val Arg Thr Lys Lys Asp Cys Ile Pro
225                 230                 235                 240

Leu Cys Gly Gln Arg Cys Lys Leu His Ser Arg Thr Asn Leu Cys Leu
                245                 250                 255

Arg Ala Cys Met Thr Cys Cys Asp Arg Cys Lys Cys Val Pro Pro Gly
                260                 265                 270

Thr Tyr Gly Asn Arg Glu Met Cys Gly Lys Cys Tyr Thr Asp Met Arg
                275                 280                 285

Thr His Arg Asn Lys His Lys Cys Pro
                290                 295

(2) INFORMATION FOR SEQ ID NO:7:

(i) SEQUENCE CHARACTERISTICS:
        (A) LENGTH: 713 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:7:

| | | | | | |
|---|---|---|---|---|---|
| GCACGACGCG | TTTCGCATTT | CGTCTTTCTC | TCTCCAATGG | CTTCTATTGC | TGGTTCATCC | 60 |
| ATCTCCATGC | AACCTTGCCC | CTTTGCTAAA | GGCAGTGTTT | CCGGGTTGAA | ATTGGGTTCA | 120 |
| TTTATGAACC | AGGGAAGAAG | CACCCTCTCA | TTTACGATGC | GTCCAATGCC | TGCTCGCTTG | 180 |
| CAGATCTGCT | GTGCTGCCAA | ACAAGAGACC | GTGGATAAGG | TATGTGAAGT | AGTAAAGAGA | 240 |
| CAATTACCTT | TACACAATGA | CAAACCAATC | ACCGGTGAAT | CAACATTTCT | TGATCTTGGA | 300 |
| GCTGATTCTC | TTGATACGGT | TGAGATTGTG | TTGGGACTTG | AGGAAGAATT | CGGAATCACG | 360 |
| GTGGAAGAGG | ACAACGCACA | ATCCATCACA | ACTGTTCAAG | ATGCTGCAGA | ACTTCTTGAG | 420 |
| AAGCTGTGCA | GTGAGAAAAG | TGCCTAGAAA | ACAAGGATCG | CAGTTGGTTG | GTTTATTTGC | 480 |
| CGATATTTGA | TATTCACATA | CTAGACCGCA | AACCCGGGGG | AAATCATGTG | TGAACTTTTA | 540 |
| TTATGTTGAA | TATGTAGGAA | ATTTCGTAAT | AAAGTTGTTG | GGATTCTTAG | TTAAATTGTG | 600 |
| GAACTTAAAA | TGTGTCATTT | CGTTTTACCG | TAGTGGTTTA | TGTAGAAGTT | TTTTGTTTAA | 660 |
| TCAAGCTGCA | TATCTCGGTT | GAGGGTTTTA | TTTCTGCTAA | AAAAAAAAAA | AAA | 713 |

(2) INFORMATION FOR SEQ ID NO:8:

(i) SEQUENCE CHARACTERISTICS:
        (A) LENGTH: 136 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ala Ser Ile Ala Gly Ser Ser Ile Ser Met Gln Pro Cys Pro Phe
 1               5                  10                  15

Ala Lys Gly Ser Val Ser Gly Leu Lys Leu Gly Ser Phe Met Asn Gln
            20                  25                  30

Gly Arg Ser Thr Leu Ser Phe Thr Met Arg Phe Met Phe Ala Arg Leu
        35                  40                  45

Gln Leu Cys Cys Ala Ala Lys Gln Glu Thr Val Asp Lys Val Cys Glu
    50                  55                  60

Val Val Lys Arg Gln Leu Pro Leu His Asn Asp Lys Pro Ile Thr Gly
65                  70                  75                  80

Glu Ser Thr Thr Leu Asp Lys Gly Ala Asp Ser Leu Asp Thr Val Glu
                85                  90                  95

Ile Val Leu Gly Leu Glu Glu Glu Phe Gly Ile Thr Val Glu Glu Asp
            100                 105                 110

Asn Ala Gln Ser Ile Tyr Tyr Val Gln Asp Ala Ala Glu Leu Leu Glu
        115                 120                 125

Lys Leu Cys Ser Glu Lys Ser Ala
    130                 135
```

(2) INFORMATION FOR SEQ ID NO:9:

(i) SEQUENCE CHARACTERISTICS:
        (A) LENGTH: 1312 base pairs
        (B) TYPE: nucleic acid
        (C) STRANDEDNESS: double
        (D) TOPOLOGY: linear (ii) MOLECULE TYPE: cDNA to mRNA -continued (xi) SEQUENCE DESCRIPTION: SEQ ID NO:9:

```
GAAGAATTCG CCAAACCACG CTAACCCAAA ACACAAGAAA AAGAAAGAAA GAAAAAAAAA      60

AGGGAATACC CCTTACCTTC ATAGAGAGAA CAAGAGAAAC AAAGCAAGGT ATTTTTTTTC     120

TTCACCTGTA AAAATGGCGT CGGCGAGTAC TTGGATATTG TCGCTAAAGT TACTTTTAAT     180

TTCTACCGGT ATATTGGGTA TAGCTTTAGG ACTTAAAATC TCTGTTCCAT GGTTTTTGG      240

AATTCTCTGT TTCTCAAGCT CCGTTATGGT GGAGTGGTTT CCGTTCTTTG GCTCAAGCCT     300

CCATATCTTT ACCGTCGTCA TCAACGGGAT CATCATCACA ATAGCAGCAT CGTCGCGGTT     360

TAACCAAAAC AACGGCGAGA AGATCAGAT GGAGCAGATG CAACCGCGGC CGAAGATCTC      420

GGAGGATCAA CAACCAATTG TGGAGTATGA TACAAAGAGC GGGTGGGGCT CCGACGCAGT     480

GGAATCCAGT GATTTCGTGT ACGAGGAAAA TCAGAGAGGA GAAGAGGTGG CAACCAGGGT     540

CTCCGAGGAG GAGAGCAATG TGGCGGTTGA AGATGACAGA GATGGAAACG AGTTTGTTAT     600

CTCTAAGTCG GAGTGGATTC CTCCAAGTAG AACGGATTCT TCGGAGATTC CGTTGGATGC     660

TCTGCTTATA CAGGAGAAAC CTGCTCCTTC TTCTAGATCC GGTCACCGGA AACCTGTTAA     720

AGTCAATCCC GAAGGTGGGC GAGCGTTGAA AGCGCGAAGC CAAAACGGCA TGAGACGCTG     780

GCAAAAACAC TTGGAAGATG ATAAACGGAG GGGAAATCAA TGCCGTTGTC CAGACACTTG     840

AAGAAGTCGG ACACGTGGGA GAATCACGGC CGTGATATCA ACGTGGAGGC ATTGACCAGC     900

TCCCCTCTGA TGAAGAAATC GGAAACGTTC AGAGACCGGA CCAATTACCA GCTGCCACCC     960

GAACAAGTAA GCTCTTTCCC GGCTTCAGGA AAGCTGAGAA AAGAACCGTC GCTGAGACAG    1020

GACGAGTTGA ATCGTCGAGT GGAAGCTTTT ATAAAGAAGT TTAATGACGA GATGAGGTTA    1080

CAGAGACAAG AATCACTTAA TCAGTACATG GAAATGGTTA ACCGTGGAAG TTAGCCACTA    1140

AACACAATAG TCCAATATCT TCTGCCATAA CCCTCAAGAG AAGAAAAGAA TATATATTAG    1200

ATTAACTTTT GGGAATATGT TTTGCTCCAA TAAATTTAAA GAGGTTGGAG ATTTGAAAGG    1260

AAAAAAAAAT CTATGCAGGG TTTTATGTTT TTGGTGGTTT GGCGAATTCT TC            1312
```

(2) INFORMATION FOR SEQ ID NO:10:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ala Ser Ala Ser Thr Trp Ile Leu Ser Leu Lys Leu Leu Leu Ile
1               5                   10                  15

Ser Thr Gly Ile Leu Gly Ile Ala Leu Gly Leu Lys Ile Ser Val Pro
            20                  25                  30

Leu Val Phe Gly Ile Leu Cys Phe Ser Ser Ser Val Met Val Glu Trp
        35                  40                  45

Phe Pro Phe Phe Gly Ser Ser Leu His Ile Phe Thr Val Val Ile Asn
    50                  55                  60

Gly Ile Ile Ile Thr Ile Ala Ala Ser Ser Arg Phe Asn Gln Asn Asn
65                  70                  75                  80

Gly Glu Lys Asp Gln Met Glu Gln Met Gln Pro Arg Pro Lys Ile Ser
                85                  90                  95

Glu Asp Gln Gln Pro Ile Val Glu Tyr Asp Thr Lys Ser Gly Trp Gly
            100                 105                 110
```

-continued

```
Ser Asp Ala Val Glu Ser Ser Asp Phe Val Tyr Glu Glu Asn Gln Arg
        115                 120             125

Gly Glu Glu Val Ala Thr Arg Val Ser Glu Glu Glu Ser Asn Val Ala
        130                 135             140

Val Glu Asp Asp Arg Asp Gly Asn Glu Phe Val Ile Ser Lys Ser Glu
145                 150                 155             160

Trp Ile Pro Pro Ser Arg Thr Asp Ser Ser Glu Ile Pro Leu Asp Ala
                165                 170             175

Leu Leu Ile Gln Glu Lys Pro Ala Pro Ser Ser Arg Ser Gly His Arg
            180                 185             190

Lys Pro Val Lys Val Asn Pro Glu Gly Gly Arg Ala Leu Lys Ala Arg
        195                 200             205

Ser Gln Asn Gly Met Arg Arg Trp Gln Lys His Leu Glu Asp Asp Lys
        210                 215             220

Arg Arg Gly Asn Gln Cys Arg Cys Pro Asp Thr
225                 230             235
```